US008778264B2

(12) United States Patent
McClung, III

(10) Patent No.: US 8,778,264 B2
(45) Date of Patent: Jul. 15, 2014

(54) FLUID TREATMENT SYSTEMS

(76) Inventor: Guy L. McClung, III, Rockport, TX (US)

( * ) Notice: Subject to any disclaimer, the term of this patent is extended or adjusted under 35 U.S.C. 154(b) by 301 days.

(21) Appl. No.: 13/317,588

(22) Filed: Oct. 21, 2011

(65) Prior Publication Data
US 2012/0103815 A1 May 3, 2012

Related U.S. Application Data

(60) Provisional application No. 61/455,886, filed on Oct. 28, 2010, provisional application No. 61/456,307, filed on Nov. 4, 2010, provisional application No. 61/459,484, filed on Dec. 13, 2010.

(51) Int. Cl.
A61L 2/00 (2006.01)
C02F 1/02 (2006.01)
B82Y 30/00 (2011.01)
C02F 1/48 (2006.01)

(52) U.S. Cl.
CPC .............. C02F 1/02 (2013.01); C02F 2209/02 (2013.01); C02F 1/484 (2013.01); C02F 2305/08 (2013.01); C02F 2303/04 (2013.01); B82Y 30/00 (2013.01)
USPC ............................................. 422/22; 422/23

(58) Field of Classification Search
CPC ................ C02F 1/00; C02F 1/34; C02F 1/48; C02F 1/4608; C02F 1/488; A61L 2/023; A61L 2/03; A61L 2/23
USPC ............ 422/22, 23; 210/600, 748.01, 748.16, 210/748.17, 748.18; 204/450, 554
See application file for complete search history.

(56) References Cited

U.S. PATENT DOCUMENTS

| 3,326,757 | A | 2/1966 | Litt | 204/149 |
| 3,266,630 | A | 8/1966 | Litt | 210/394 |
| 4,195,629 | A | 4/1980 | Halford | 128/206.13 |
| 4,759,857 | A | 7/1988 | Acuna | 210/741 |
| 4,895,558 | A | 1/1990 | Cham | 604/5.03 |
| 4,966,140 | A | 10/1990 | Herzberg | 128/206.19 |
| 5,006,264 | A | 4/1991 | Acuna | 210/741 |
| 5,099,525 | A | 3/1992 | Millauro | 2/9 |
| 5,330,559 | A | 7/1994 | Chebey et al. | 95/63 |
| 5,429,594 | A | 7/1995 | Castle | 604/4 |
| 5,462,665 | A | 10/1995 | Green | 210/496 |
| 5,573,577 | A | 11/1996 | Jaonnou | 96/66 |
| 5,630,926 | A * | 5/1997 | Thompson | 204/665 |

(Continued)

FOREIGN PATENT DOCUMENTS

EP 0685987 A2 * 12/1995 ............... H05B 3/00

OTHER PUBLICATIONS

"High Speed Water Sterlization Using One-Dimensional Nanostructures," Schoen et al; Nano Letters, American Chemical Society, pp. 3628-3632, Aug. 20, 2010.
"Silver threads of life," The Economist, Oct. 21, 2010, 2pp.

Primary Examiner — Regina M Yoo
(74) Attorney, Agent, or Firm — Guy McClung

(57) ABSTRACT

Systems and methods for treating a fluid by passing fluid through a treatment structure, the fluid containing undesirable living things, the treatment structure containing electrically conductive nanomaterial with silver, flowing an electric current in the fluid in the treatment structure via the electrically conductive nanomaterial with silver or silver material to kill undesirable living things in the treatment structure, and killing undesirable things in the treatment structure.

13 Claims, 11 Drawing Sheets

(56) References Cited

U.S. PATENT DOCUMENTS

| | | | |
|---|---|---|---|
| 5,807,425 A | 9/1998 | Gibbs | 96/66 |
| 5,846,302 A | 12/1998 | Putro | 96/66 |
| 6,764,533 B2 | 7/2004 | Lobiondo, Jr. | 96/66 |
| 7,135,195 B2 | 11/2006 | Holladay et al. | 424/618 |
| 7,258,689 B2 | 8/2007 | Salvo | 606/41 |
| 7,355,216 B2 | 4/2008 | Yang et al. | 257/200 |
| 7,419,601 B2 * | 9/2008 | Cooper et al. | 210/679 |
| 7,655,148 B2 | 2/2010 | Chen et al. | 210/688 |
| 7,815,806 B2 | 10/2010 | Cooper et al. | 210/660 |
| 7,829,622 B2 | 11/2010 | McDaniel et al. | 524/496 |
| 7,834,139 B2 | 11/2010 | Matsui et al. | 530/300 |
| 2003/0032892 A1 | 2/2003 | Erlach et al. | 600/547 |
| 2004/0005242 A1 * | 1/2004 | Koulik et al. | 422/22 |
| 2009/0145737 A1 | 6/2009 | Kamen et al. | 202/185.1 |
| 2009/0269249 A1 | 10/2009 | Nakajima et al. | 422/122 |
| 2010/0000770 A1 | 1/2010 | Gupta et al. | 174/255 |
| 2011/0303543 A1 * | 12/2011 | Fritze | 204/554 |

* cited by examiner

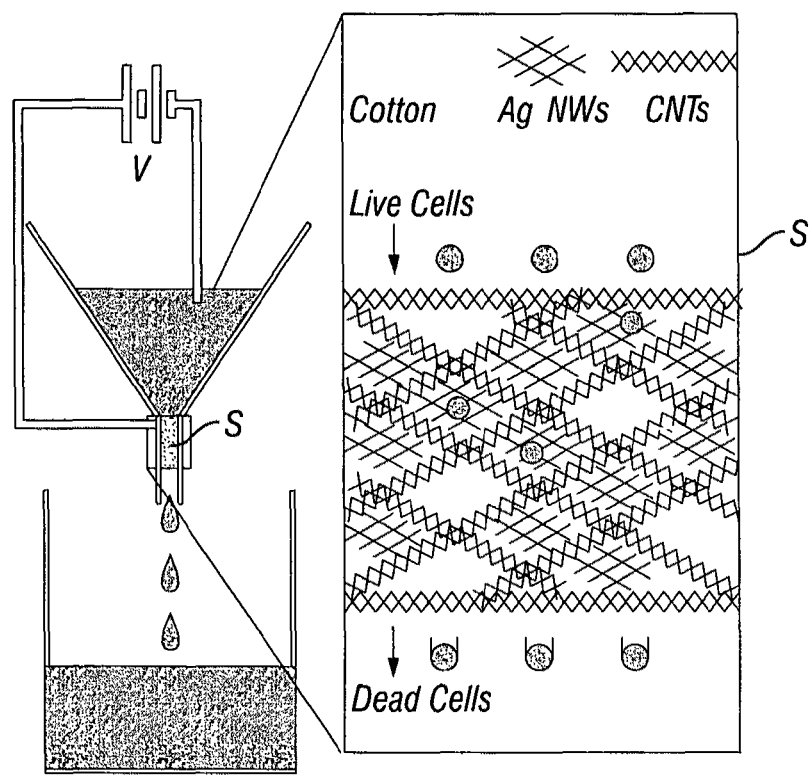
FIG. 1
*(Prior Art)*
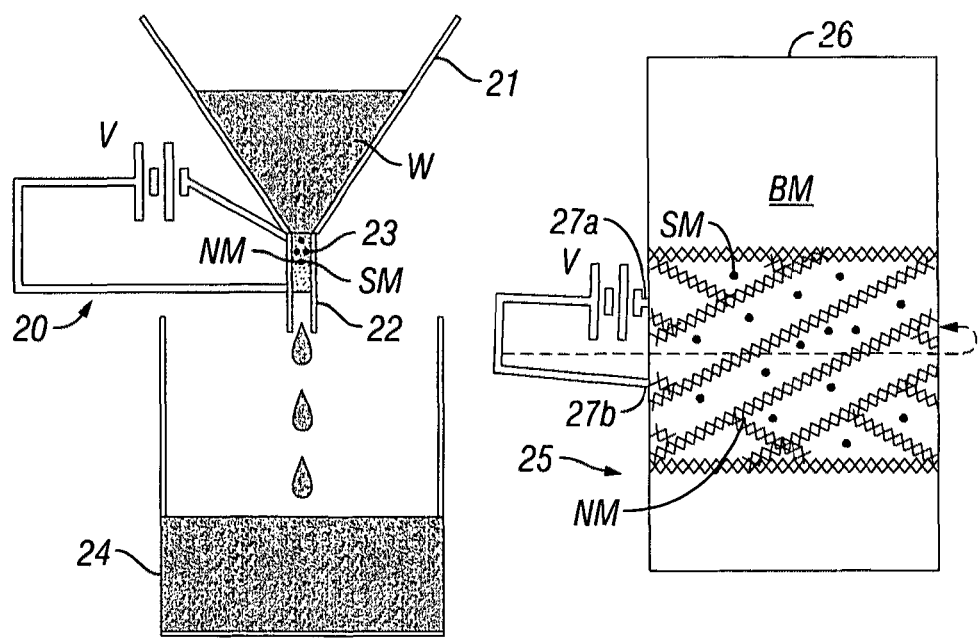
FIG. 2       FIG. 2A

FLUID TREATMENT SYSTEMS

CROSS REFERENCE TO RELARED APPLICATIONS

The present invention and application claim priority under the United States patent Laws from U.S. Applications Ser. Nos. 61/455,886 filed Oct. 28, 2010; 61/456,307 filed Nov. 4, 2010; and 61/459,484 filed Dec. 13, 2010, all said applications incorporated fully herein for all.

BACKGROUND OF THE INVENTION

1. Field of the Invention

The present invention is directed to systems and methods for treating fluids; to such systems and methods for purifying water; and, in certain particular aspects, to systems and methods for purifying water using electrical current passed through the water to kill undesirable things in the water, the current flowing via electrically conductive nanomaterial in a treatment structure though which the water flows; and in certain aspects, such systems and methods in which undesirable things are killed by the biocidal effects of silver.

2. Description of Related Art

FIG. 1 illustrates a prior art system and method as disclosed in "High Speed Water Sterilzation Using One-Dimensional Nanostructures" by Schoen et al, American Chemical Society, 2010, pages 3628-3632 which describes a "gravity-fed biofouling resistant device that can inactivate bacteria". Water flows from a container, through a structure S, and down by gravity into a collection container. The structure S is made of cotton and has silver nanowires ("AgNWs") and carbon nanotubes ("CNTs"). The carbon nanotubes provide electrical conductivity over the active area of the structure when a current is imposed on it with a power source ("V"). Silver was chosen since it is a well-known bactericidal agent. The device was operated at five separate biases from −20 to +20 volts and a copper mesh counterelectrode was held at ground at approximately one centimeter from the structure.

BRIEF SUMMARY OF THE INVENTION

The present invention, in certain aspects, discloses systems and methods for treating fluids, e.g., but not limited to, water and air; such systems and methods for killing things in fluids, e.g., but not limited to, killing bacteria, viruses, algae and/or fungi; in certain aspects, such systems and methods which employ fluid movement by mechanisms or action other than, or in addition to, gravity feed; and such systems and methods in which a treatment structure through which the fluid flows has silver or silver alloy material and electrically conductive nanomaterial which, when an appropriate potential difference is applied across it, results in a current flow and in a lethal current being applied to living thing(s) in the fluid flowing through the treatment structure.

In certain embodiments of systems and methods according to the present invention, undesirable things are killed by the biocidal effects of silver. In certain particular aspects, silver is provided with electrically conductive nanomaterial; in some aspects such nanomaterial in combination with another source of silver; and in other aspects with another source or silver and/or with a solution of colloidal silver. In certain embodiments of systems and methods according to the present invention, liquids are moved by capillary action, siphonage, and/or by moving structures; while in other aspects when silver is provided by nanomaterial with silver therein or thereon (with or without silver wires, pieces, or the like) gravity fed liquid is employed.

In certain embodiments of systems and methods according to the present invention, fluid is heated by imposing an electrical current on electrically conductive nanomaterial in the liquid thereby resistively heating the nanomaterial and, in turn, heating the liquid. In one particular aspect, the liquid is heated sufficiently to kill undesirable things in the liquid. In certain aspects, the current is applied by applying a potential difference across a treatment structure according to the present invention.

"Electrically conductive nanomaterial" includes any known nanomaterial which can conduct electricity and which is present in treatment structures according to the present invention insufficient amount, dispersion and concentration so that things in fluid being treated are killed by a current passing through the treatment structure via the electrically conductive nanomaterial; the electrically conductive nanomaterial including, but not limited to, electrically conductive nanotubes, nanorods, nanowires, nanoparticles, nanostructures, nanofibers, nanofabric, nanocylinders, nanographene, nanographene ribbons, transformed nanomaterials, functionalized nanomaterial, metallized nanomaterial, carbon nanomaterials, e.g., but not limited to, carbon nanotubes, and electrically conductive nanotubes including single walled nanotubes, multi-walled nanotubes, functionalized nanotubes and metallized nanotubes. "Electrically conductive nanomaterial with silver" is any "electrically conductive nanomaterial" with silver thereon and/or therein and/or combined therewith which silver acts as a silver ion donor to provide silver ions for killing undesirable things, including, but not limited to nanomaterial metallized with, coated with, or plated with silver or silver alloy(s), including, but not limited to, nanotubes with such metallization, plating, or coating and/or nanotubes with protection material that is silver added or applied as in, for example, any of the methods for protecting nanotubes with protective material disclosed in U.S. application Ser. No. 12/638,999 filed Nov. 14, 2008. The electrical conductive nanomaterial is added to and dispersed in a fluid by any suitable known means, including, but not limited to, mixing, pouring, blending, stirring, and sonication.

"Silver material" includes silver and silver alloys present in sufficient amounts, dispersion and concentration so that the killing effects of silver for killing certain living things are achieved; including, but not limited to, silver, silver alloys, argentium (either 93.5% minimum silver content and 96% minimum silver content, billion, silver electrum, goloid (including, but not limited to, as in U.S. Pat. No. 191,146), britannia silver, shibuichi, sterling silver, and tibetan silver, or some combination of two, three or more of these and silver and silver materials that provide a desired amount of the bioactive silver ion Ag+. The silver material can be present in any form, e.g., but not limited to, as particles, granules, wires, pieces, discs, fiber, fabric, mesh, or in solution.

Accordingly, the present invention includes features and advantages which are believed to enable it to advance fluid treatment technology. Characteristics and advantages of the present invention described above and additional features and benefits will be readily apparent to those skilled in the art upon consideration of the following detailed description of preferred embodiments and referring to the accompanying drawings.

What follows are some of, but not all, the objects of this invention. In addition to the specific objects stated below for at least certain preferred embodiments of the invention, there are other objects and purposes which will be readily apparent to one of skill in this art who has the benefit of this invention's teachings and disclosures. It is, therefore, an object of at least certain preferred embodiments of the present invention to provide:

New, useful unique, efficient, nonobvious systems and methods for treating fluids to kill things in fluid such as, but not limited to, bacteria, algae, fungi and viruses using silver and/or lethal electric current flowing via electrically conductive nanomaterial;

Such new, useful, unique, efficient, nonobvious systems and methods using fluid movement by mechanisms or action other than, or in addition to, gravity feed;

Such new, useful unique, efficient, nonobvious systems and methods in which liquids are moved by capillary action, siphonage, upflow, and/or by moving structures; and New, useful unique, efficient, nonobvious systems and methods for treating fluids in which an electric potential difference is imposed on electrically conductive nanomaterial within a structure through which the fluid flows, so that electric current flows for killing things in the fluid; the structure, optionally, also containing silver and/or silver alloy(s); and such systems and methods in which liquid passing through structures according to the present invention is heated by the resistive heating of electrically conductve nanomaterial within a treatment structure according to the present invention; and such systems and methods in which structures according to the present invention through which fluids flow have pores with pores sizes sufficiently large that the fluid is not filtered and/or with pores sizes that are sufficiently small that the fluid is filtered; and, in certain aspects, a treatment structures is a filter elements or filter cartridge;

Such new, useful unique, efficient, nonobvious systems and methods in which treated fluids are passed through secondary structure for removing things killed within a primary structure and/or secondary structure for removing nanomaterial from treated fluid (either of which can be true for any base material disclosed herein.

Such new, useful, unique, efficient, nonobvious systems and methods in which nanomaterials are removed from treated fluids and, in one aspect, nanomaterials are used which have or which are combined with magnetic material so that magnet (s) and/or magnet apparatus are used for removing the nanomaterials from treated fluid.

Certain embodiments of this invention are not limited to any particular individual feature disclosed here, but include combinations of them distinguished from the prior art in their structures, functions, and/or results achieved. Features of the invention have been broadly described so that the detailed descriptions that follow may be better understood, and in order that the contributions of this invention to the arts may be better appreciated. There are, of course, additional aspects of the invention described below and which may be included in the subject matter of the claims to this invention. Those skilled in the art who have the benefit of this invention, its teachings, and suggestions will appreciate that the conceptions of this disclosure may be used as a creative basis for designing other structures, methods and systems for carrying out and practicing the present invention. The claims of this invention are to be read to include any legally equivalent devices or methods which do not depart from the spirit and scope of the present invention.

The present invention recognizes and addresses the long-felt needs and provides a solution to problems and a satisfactory meeting of those needs in its various possible embodiments and equivalents thereof. To one of skill in this art who has the benefits of this invention's realizations, teachings, disclosures, and suggestions, other purposes and advantages will be appreciated from the following description of certain preferred embodiments, given for the purpose of disclosure, when taken in conjunction with the accompanying drawings. The detail in these descriptions is not intended to thwart this patent's object to claim this invention no matter how others may later disguise it by variations in form, changes, or additions of further improvements.

It will be understood that the various embodiments of the present invention may include one, some, or all of the disclosed, described, and/or enumerated improvements and/or technical advantages and/or elements in claims to this invention.

BRIEF DESCRIPTION OF THE SEVERAL VIEWS OF THE DRAWING

A more particular description of embodiments of the invention briefly summarized above may be had by references to the embodiments which are shown in the drawings which form a part of this specification. These drawings illustrate embodiments preferred at the time of filing for this patent and are not to be used to improperly limit the scope of the invention which may have other equally effective or legally equivalent embodiments.

FIG. 1 is a schematic view of prior art system.

FIG. 2 is a schematic view of a system according to the present invention.

FIG. 2A is a schematic view of a system according to the present invention.

Figure 1A:
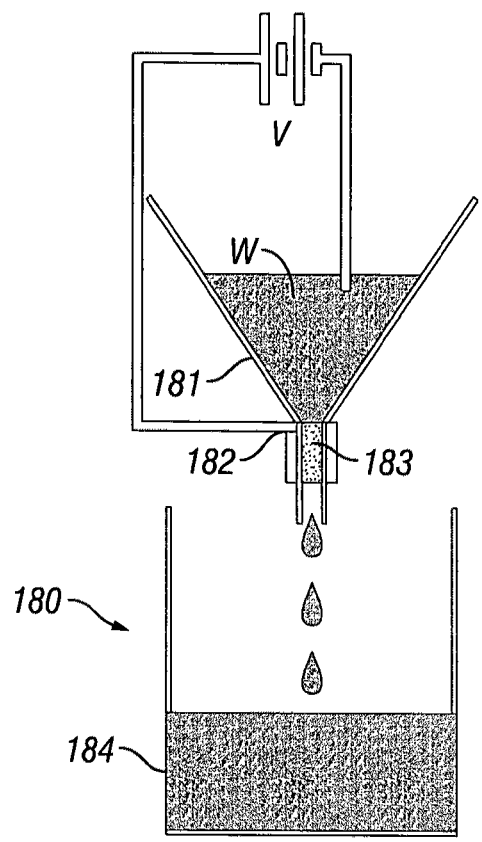
FIG. 1A is a schematic view of a system according to the present invention.

Certain embodiments of the invention are shown in the above-identified figures and described in detail below. Various aspects and features of embodiments of the invention are described below. Any combination of aspects and/or features described below can be used except where such aspects and/or features are mutually exclusive. It should be understood that the appended drawings and description herein are of certain embodiments and are not intended to limit the invention. On the contrary, the intention is to cover all modifications, equivalents and alternatives falling within the spirit and scope of the invention as defined by the appended claims. In showing and describing these embodiments, like or identical reference numerals are used to identify common or similar elements. The figures are not necessarily to scale and certain features and certain views of the figures may be shown exaggerated in scale or in schematic in the interest of clarity and conciseness.

As used herein and throughout all the various portions (and headings) of this patent, the terms "invention", "present invention" and variations thereof mean one or more embodiments, and are not intended to mean the claimed invention of any particular embodiment. Accordingly, the subject or topic of each such reference is not automatically or necessarily part of, or required by, any particular embodiment. So long as they are not mutually exclusive or contradictory any aspect or feature or combination of aspects or features of any embodiment disclosed herein may be used in any other embodiment disclosed herein.

DETAILED DESCRIPTION OF THE INVENTION

Unless explicitly stated otherwise, treatment structures according to the present invention in embodiments described below have base material, electrically conductive nanomaterial and, optionally, silver or silver material. Current flowing in the treatment structure via the electrically conductive nanomaterial kills living thing(s) in fluid flowing through the treatment structure and, when present, silver ions contributed by the silver material also act to kill the living thing(s).

The present invention provides methods for treating a fluid, the methods including: passing fluid through a treatment structure, the fluid containing undesirable living things, the treatment structure containing electrically conductive nanomaterial with silver or silver material in a base material, the fluid, optionally, containing silver material, the treatment structure, optionally, containing silver material other than silver in or on nanomaterial, the methods including flowing an electric current in the fluid in the treatment structure via the electrically conductive nanomaterial with silver or silver material to kill undesirable living things in the treatment structure, and killing undesirable things in the treatment structure. Such methods may have one or some, in any possible combination, of the following: wherein the fluid is water; wherein the fluid passes through the treatment structure by the force of gravity; wherein the fluid passes through the treatment structure by siphoning; wherein the fluid passes through the treatment structure by pumping; wherein the treatment structure is moved through the fluid so that the treatment structure takes in fluid and said fluid passes through the treatment structure for treating thereby; wherein electric current flows through substantially all, of the treatment structure; wherein electric current flows through a portion of the treatment structure; wherein the treatment structure contains base material and the electrically conductive nanomaterial with silver or silver material is in the base material; wherein the base material is one of nylon, plastic, fibers, granular media, fabric, fibril materials, filamentous materials, inorganic or organic materials, biological organism selective materials, natural or synthetic materials, cotton, wool, polyester, fiber glass, metal, woven or nonwoven, air laid web material, sheets of material, interleaved sheets, material with pores or openings or pore sizes such that it does not filter fluid or material with pores or openings or pore sizes of such dimensions that fluid is filtered, material containing silver and/or silver material; wherein the nanomaterial is one of nanotubes, nanorods, nanowires, nanoparticles, nanostructures, nanofibers, nanofabric, nanocylinders, nanographene, nanographene ribbons, transformed nanomaterials, functionalized nanomaterial, metallized nanomaterial, carbon nanomaterials, carbon nanotubes, single walled nanotubes, multi-walled nanotubes, functionalized nanotubes and metallized nanotubes; flowing treated fluid from the treatment structure; wherein the treated fluid contains dead things killed in the treatment structure, the method further including removing dead things from the treated fluid; wherein the treated fluid contains nanomaterial, the method further including removing nanomaterial from the treated fluid; wherein the removed nanomaterial contains magnetically attractive material, the method further including removing the nanomaterial containing magnetically attractive material with magnet apparatus; wherein the magnet apparatus is one of magnet, at least one magnet, a plurality of magnets, an electromagnet apparatus, at least one electromagnet apparatus, and a plurality of electromagnet apparatuses; wherein magnet apparatus is within the treatment structure, adjacent the treatment structure, within a member through which the treated fluid passes, or within a container containing the treated fluid; wherein the electric current heats fluid in the treatment structure; wherein the electric current boils fluid in the treatment structure; and/or wherein the electric current heats fluid in the treatment structure thereby killing living things in the fluid.

The present invention provides methods for treating a fluid which include: passing fluid through a treatment structure, the fluid containing undesirable living things, the treatment structure containing electrically conductive nanomaterial with silver or silver material, flowing an electric current in the fluid in the treatment structure via the electrically conductive nanomaterial with silver to kill undesirable living things in the treatment structure, killing undesirable things in the treatment structure producing treated fluid, flowing the treated fluid back to the treatment structure, passing the treated fluid through the treatment structure, flowing an electric current in the treated fluid in the treatment structure via the electrically conductive nanomaterial with silver or silver material to kill undesirable living things in the treatment structure.

The present invention provides methods for treating a fluid which include: passing fluid through a treatment structure, the fluid containing undesirable living things, the treatment structure containing electrically conductive nanomaterial, the fluid containing silver or silver material, flowing an electric current in the fluid in the treatment structure via the electrically conductive nanomaterial to kill undesirable living things in the treatment structure, and killing undesirable things in the treatment structure, wherein the fluid is moved through the treatment structure by siphoning or by pumping or wherein the treatment structure is moved through the fluid. In such a method the electrically conductive nanomaterial may include electrically conductive nanomaterial with silver.

The present invention provides methods for treating a fluid which include: passing fluid through a treatment structure, the fluid containing undesirable living things, the treatment structure containing electrically conductive nanomaterial, the fluid containing silver or silver material, flowing an electric current in the fluid in the treatment structure via the electrically conductive nanomaterial silver to kill undesirable living things in the treatment structure, the electric current passing through only a portion of the treatment structure, killing undesirable things in the treatment structure. In such a method, the electrically conductive nanomaterial may include electrically conductive nanomaterial with silver or silver material.

The present invention provides methods for treating a fluid which include: passing fluid through a treatment structure, the fluid containing undesirable living things, the treatment structure containing electrically conductive nanomaterial, the fluid containing silver or silver material, flowing an electric current in the fluid in the treatment structure via the electrically conductive nanomaterial silver to kill undesirable living things in the treatment structure, killing undesirable things in the treatment structure, flowing treated fluid from the treatment structure, and removing dead things from the treated fluid. In such a method, the electrically conductive nanomaterial may include electrically conductive nanomaterial with silver or silver material.

The present invention provides methods for treating a fluid which include: passing fluid through a treatment structure, the fluid containing undesirable living things, the treatment structure containing electrically conductive nanomaterial, the fluid containing silver or silver material, flowing an electric current in the fluid in the treatment structure via the electrically conductive nanomaterial silver to kill undesirable living things in the treatment structure, killing undesirable things in the treatment structure, removing nanomaterial from the treated fluid. In such a method, the electrically conductive nanomaterial may include electrically conductive nanomaterial with silver or silver material; and, optionally, the removed nanomaterial contains magnetically attractive material, the method further including removing the nanomaterial containing magnetically attractive material with magnet apparatus. In such a method, the magnet apparatus may be one of magnet, at least one magnet, a plurality of magnets, an electromagnet apparatus, at least one electromagnet apparatus, and a plurality of electromagnet apparatuses and/or the magnet apparatus may be within the treatment structure, adjacent the treatment structure, within a member through which the treated fluid passes, or within a container containing the treated fluid.

The present invention provides methods for treating a fluid which include: passing fluid through a treatment structure, the fluid containing undesirable living things, the treatment structure containing electrically conductive nanomaterial, the fluid containing silver or silver material, flowing an electric current in the fluid in the treatment structure via the electrically conductive nanomaterial silver to kill undesirable living things in the treatment structure, killing undesirable things in the treatment structure, wherein the electric current heats the electrically conductive nanomaterial which heats fluid in the treatment structure. Such a method may include one or some, in any possible combination, of the following: wherein the electric current boils fluid in the treatment structure; wherein the electric current heats fluid in the treatment structure thereby killing living things in the fluid; and/or wherein the electrically conductive nanomaterial includes electrically conductive nanomaterial with silver or silver material.

The present invention provides methods for treating a fluid which include: passing fluid through a treatment structure, the fluid containing undesirable living things, the treatment structure containing electrically conductive nanomaterial, flowing an electric current in the fluid in the treatment structure via the electrically conductive nanomaterial material to kill undesirable living things in the treatment structure, killing undesirable things in the treatment structure producing treated fluid, flowing the treated fluid back to the treatment structure, passing the treated fluid through the treatment structure, flowing an electric current in the treated fluid in the treatment structure via the electrically conductive nanomaterial to kill undesirable living things in the treatment structure. In such a method, the electrically conductive nanomaterial may include electrically conductive nanomaterial with silver or silver material.

The present invention provides treatment structures for fluids which include therein electrically conductive nanomaterial with silver or silver material. Optionally, such a structure includes a power source for applying current to the nanomaterial to kill things in the fluid, e.g., but not limited to, a battery or a solar power source. In any system herein, a power source may be located as desired, including, but not limited to, location outside of nanomaterial, adjacent nanomaterial, in or adjacent base material used with nanomaterial, in or adjacent filter material used with nanomaterial, within nanomaterial, on or adjacent a container or housing for a treatment structure, and/or on or within a filter cartridge with nanomaterial therein.

FIG. 1A shows a system 180 according to the present invention which has a fluid to be treated, e.g. water W, in a first container 181 which flows to an outlet 182 in which is disposed a structure 183 according to the present invention through which treated water W flows down into a second container 184. A power source V imposes a voltage so that a current flows between the top of the structure and the bottom thereof to kill things within the water that pass through the structure.

Figure 1B:
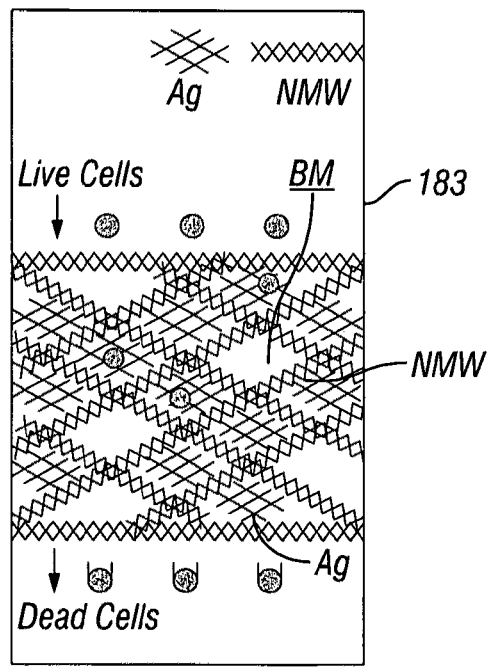
FIG. 1B is an enlargement of part of the system of FIG. 1A.

The structure 183 (enlarged in FIG. 1B) has base material BM (any disclosed herein) in which is dispersed multiple pieces of electrically conductive nanomaterial with silver or silver material NMW. Optionally, other silver ion donor material Ag (e.g., but not limited to, the wires of FIG. 1) is used dispersed in the base material BM. Optionally, with or without the material Ag present, colloidal silver solution (any disclosed herein) is added to the liquid in the first container 181 and/or into the liquid in the second container 184 (as may be done in any system according to the present invention with any second container receiving liquid by gravity feed and/or into any container into which liquid moves, is moved or is siphoned). Any power source disclosed herein connected in any manner disclosed herein may be used with the structure 183.

It is within the scope of the present invention to delete the silver material SM (e.g., to delete the silver material SM from any of the embodiments of FIGS. 2-17) and to use electrically conductive nanomaterial with silver in the systems and methods to kill undesirable things in fluids. In certain particular aspects, the electrically conductive nanomaterial with silver is metallized nanotubes including silver or silver material; functionalized nanotubes with silver; coated nanotubes coated with silver or silver material; electrically conductive nanotubes with protective material that is silver or silver material, including, but not limited to, carbon nanotubes protected with silver or silver material which is added, applied or included as protective material is combined with nanotubes as disclosed in U.S. application Ser. No. 12/738,999 filed Nov. 14, 2008 (incorporated fully herein for all purposes), whether or not such application teaches the use of silver or silver material as a protective material and including, but not limited to, mixing nanotubes with silver or silver material, comminuting nanotubes with silver or silver material, grinding nanotubes with silver or silver material, pulverizing nanotubes with silver or silver material, combining nanotubes with silver or silver material or blending nanotubes with silver or silver material; or plated nanotubes plated with silver or silver material. It is also within the scope of this invention to delete the silver wires AgNws from the system of FIG. 1 and to use for the carbon nanotubes some nanomaterial with silver as disclosed or referred to herein.

FIG. 2 shows a system 20 according to the present invention which has a fluid to be treated, e.g. water W, in a first container 21 which flows to an outlet 22 in which is disposed a structure 23 through which the water W flows down into a second container 24. A power source V imposes a voltage across the structure 23 so that a current flows between the top of the structure and the bottom thereof to kill things within the water that passes through the structure. As is true for each embodiment described as having "silver material SM", the structure 23 has silver material SM which may be any possible silver material as described herein.

As is true for any embodiment of the present invention and for any treatment structure according to the present invention, the power source V may be any suitable known apparatus, device, or system that can impose a potential difference across the structure 23 or across part of the structure 23, including, but not limited to, conventional power source, a battery, solar power system or generator, generator, wind power system, or combination thereof. As is true for any embodiment of the present invention and for any treatment structure according to the present invention, the structure 23 may be a structure like any disclosed herein. In one aspect, the structure 23 is like the structure S. Optionally, the structure 23 has electrically conductive nanomaterial NM (not shown to scale). A base material of the structure 23 and a base material BM of the structure 26 (as is true for any base material BM indicated in other drawing figures) may be, but is not limited to, nylon, plastic, fibers, granular media, fabric, fibril materials, filamentous materials, inorganic or organic materials, biological organism selective materials, natural or synthetic materials, e.g., including but not limited to cotton, wool, polyester, fiber glass, metal, or blends or mixtures thereof; and fabric base material can be woven or nonwoven (e.g. air laid webs), or mixtures or combinations of sheets or portions thereof or interleaved sheets thereof. The base material BM can have openings or pore sizes such that it does not filter fluid passing through a structure containing it or it can have openings or pore sizes of such dimensions that fluid flowing through a treatment structure is filtered.

FIG. 2A shows a system 25 according to the present invention with a treatment structure 26 and a power source V (like the power source in FIG. 2). The structure 26 may be a treatment structure like any disclosed herein. The power source has leads 27a, 27b which are connected to points on the structure 26 spaced-down and apart from the top (lead 27a) and up and spaced-apart from the bottom (lead 27b). The power source imposes an electrical potential difference on part of the structure and a current flows through electrically conductive nanomaterial NM. This current kills things in fluid passing through the structure 26. Optionally, and as is true for any possible connection of leads, connectors, cables, etc. for transmitting electric current, the leads etc. used may be on the same side or portion of a treatment structure or, e.g. as shown by the dotted line for the lead 27b in FIG. 2A, they may be on opposed sides or portions of a treatment structure. As is rue for any embodiment herein, the nanomaterial NM may be nanomaterial with silver.

Figure 3:
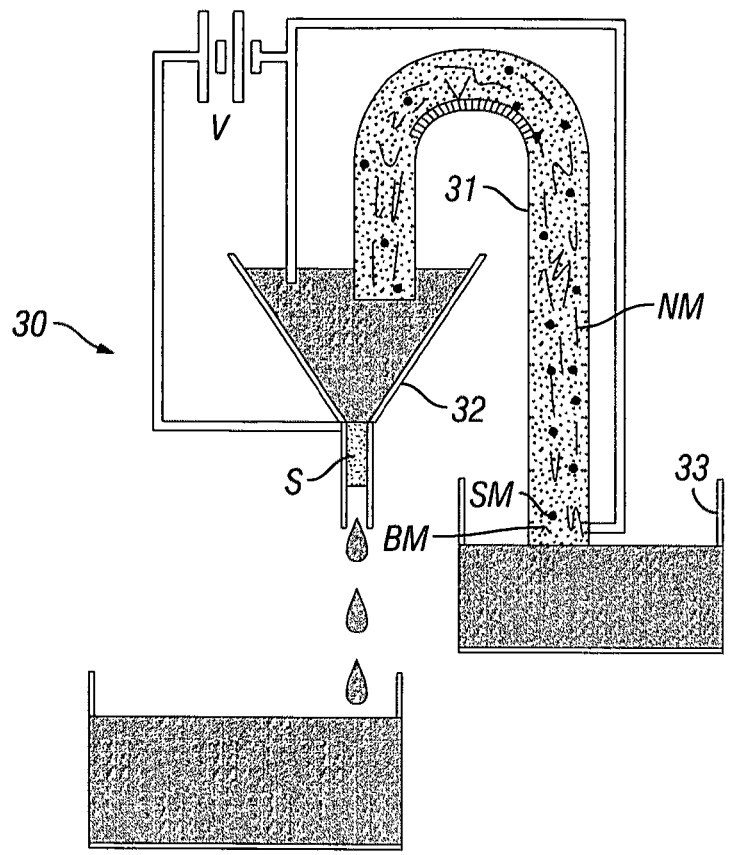
FIG. 3 is a schematic view of a system according to the present invention.

FIG. 3 shows a system 30 according to the present invention that includes some parts which are like those of the system of FIG. 1 (and like labels indicate like parts) and new items according to the present invention. In addition to a structure S, the system 30 includes a treatment structure 31 which siphons fluid from a primary container 32 into a secondary container 33. The power source V provides a bias across the structure 31 so that a current flows therethrough to kill things. Optionally, a separate power source is provided for the structure 31. The structure 31 may—as is true for any structure according to the present invention—be like any structure according to the present invention and/or be made of material(s) like that of any treatment structure according to the present invention. The power source imposes an electrical potential difference and a current flows via electrically conductive nanomaterial NM (not shown to scale). No nanomaterial shown in the drawings is to scale.

Figure 4:
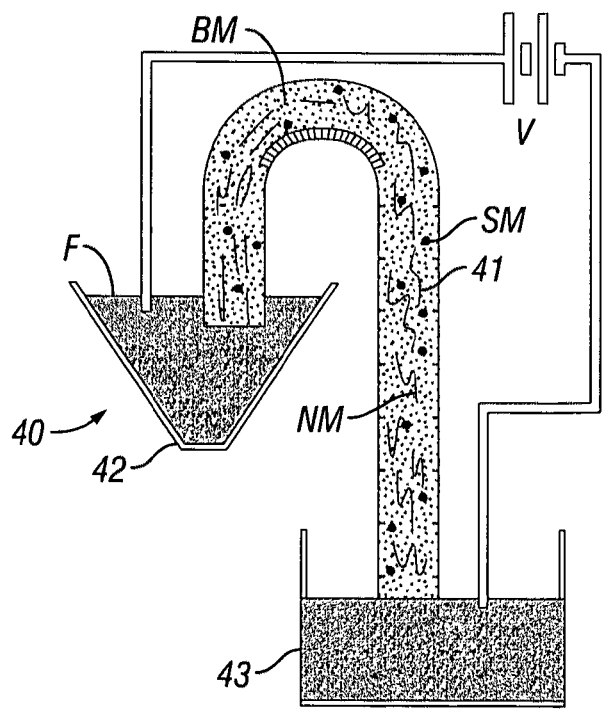
FIG. 4 is a schematic view of a system according to the present invention.

FIG. 4 shows a system 40 according to the present invention which has a treatment structure 41 which siphons fluid F from a primary container 42 into a secondary container 43. A power source V (e.g., like any disclosed herein) provides a voltage difference across the structure 41, via fluid in the container 42 and fluid in the container 43 so that a current flows therethrough to kill things passing through the structure 41. The power source imposes an electrical potential difference on the structure and a current flows via electrically conductive nanomaterial NM (not shown to scale).

Figure 5:
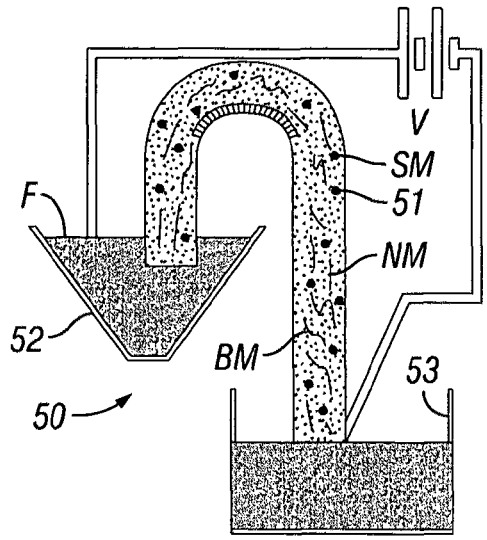
FIG. 5 is a schematic view of a system according to the present invention.

FIG. 5 shows a system 50 according to the present invention which has a treatment structure 51 which siphons fluid F from a primary container 52 into a secondary container 53. A power source V (e.g., like any disclosed herein) provides a voltage difference across the structure 51, via fluid in the container 52 and via a connection to the bottom of the structure 51 so that a current flows therethrough to kill things passing through the structure 51. The power source imposes an electrical potential difference on the structure and a current flows via electrically conductive nanomaterial NM (not shown to scale).

Figure 6:
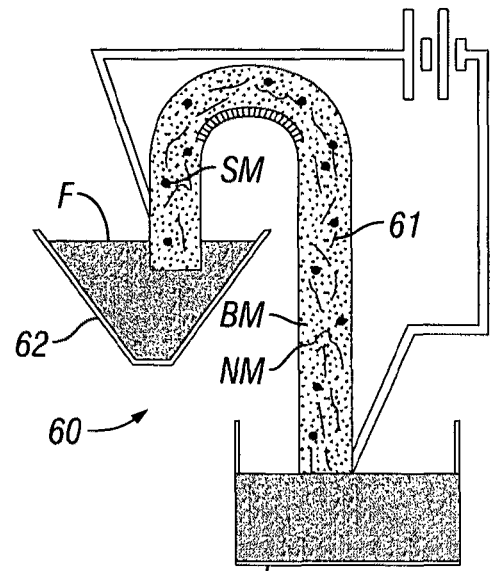
FIG. 6 is a schematic view of a system according to the present invention.

FIG. 6 shows a system 60 according to the present invention which has a treatment structure 61 which siphons fluid F from a primary container 62 into a secondary container 63. A power source V (e.g., like any disclosed herein) provides a voltage difference across the structure 61, via a connection to the structure 61 above the fluid in the container 52 and via a connection to the bottom of the structure 61 so that a current flows therethrough to kill things passing through the structure 61. The power source imposes an electrical potential difference on the structure and a current flows via electrically conductive nanomaterial NM (not shown to scale).

Figure 7:
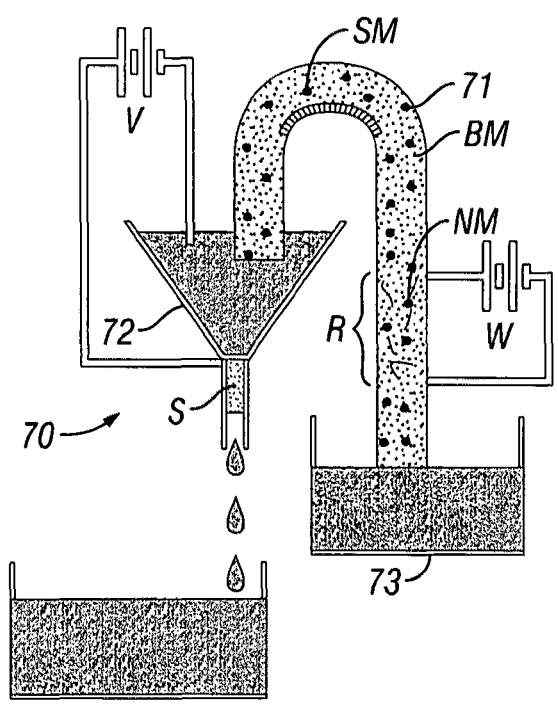
FIG. 7 is a schematic view of a system according to the present invention.

FIG. 7 shows a system 70 according to the present invention that includes some parts which are like those of the system of FIG. 1 (and like labels indicate like parts) and new items according to the present invention. In addition to a structure S, the system 70 includes a treatment structure 71 which treats and siphons fluid from a primary container 72 into a secondary container 73. A power source W (like any disclosed herein) provides a bias across part of the structure 71 so that a current flows therethrough to kill things. The structure 71 may—as is true for any structure according to the present invention—be like any structure according to the present invention and/or be made of material(s) like that of any treatment structure according to the present invention. The power source W provides the potential difference across a discrete portion R of the structure 71. The power source imposes an electrical potential difference on part of the structure and a current flows via electrically conductive nanomaterial NM (not shown to scale) which is in the part R of the structure 71.

Figure 8:
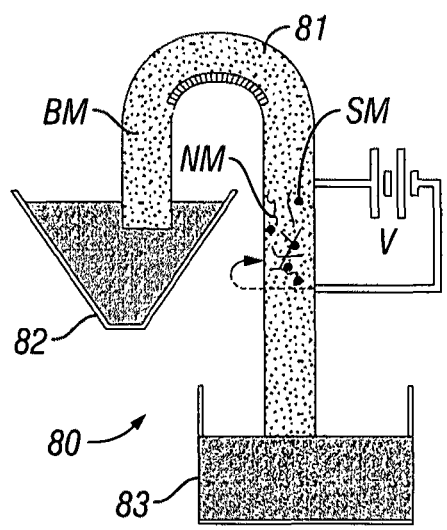
FIG. 8 is a schematic view of a system according to the present invention.

FIG. 8 shows a system 80 according to the present invention that includes a treatment structure 81 which treats and siphons fluid from a primary container 82 into a secondary container 83. A power source V (like any disclosed herein) provides a bias across part of the structure 81 so that a current flows therethrough to kill things. The structure 81 may—as is true for any structure according to the present invention—be like any structure according to the present invention and/or be made of material(s) like that of any treatment structure according to the present invention. The power source V provides the potential difference across a discrete portion of the structure 81 that has nanomaterial NM therein. The power source imposes an electrical potential difference on part of the structure and a current flows via the electrically conductive nanomaterial NM (not shown to scale).

Figure 9:
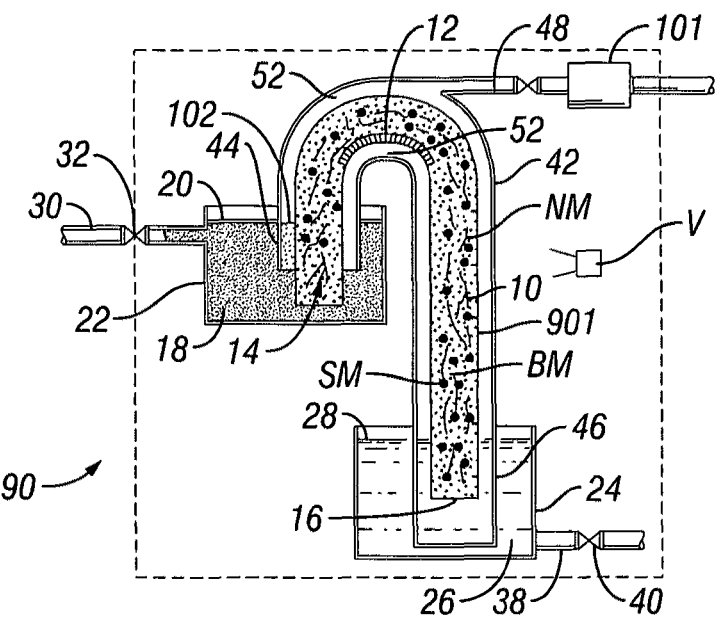
FIG. 9 is a schematic view of a system according to the present invention.

FIG. 9 shows a system 90 according to the present invention that includes a treatment structure 901 according to the present invention with base material BM with electrically conductive nanomaterial NM therein. Optionally the structure 901 includes silver material SM (not shown to scale; indicated by dots). The base material BM can be, but is not limited to, nylon, plastic, fibers, granular media, fabric, fibril materials, filamentous materials, inorganic or organic materials; biological organism selective materials natural or synthetic materials; e.g., including but not limited to cotton, wool, polyester, fiber glass, metal, or blends or mixtures thereof. The fabric can be woven or nonwoven (e.g. air laid webs), or mixtures or combinations of sheets or portions thereof or interleaved sheets thereof. The base material can have openings or pore sizes such that it does not filter fluid passing through a structure containing it or it can have openings or pore sizes of such dimensions that fluid flowing through a treatment structure is filtered. The structure 901 has an intake end 14, a discharge end 16, and an optional support element 12. The structure 901 is placed between an upper vessel 22 and a lower vessel 24 with the intake end 14 not in contact with the bottom of the upper vessel 22 or in contact therewith. The discharge end 16 may or may not contact the bottom of lower vessel 24.

The lower vessel 24 is below vessel 22. Siphoning action is maintained between a liquid 18 (e.g., water) contained in the vessel 22 and the liquid 28 that has flowed into the vessel 24. A valve 32 (in an inlet 30) opens; the liquid is introduced into vessel 22 until a liquid level 20 is close to a top of the vessel 22; then, the valve 32 closes. The liquid 18 wets the intake end 14 and enters the structure 901 at the liquid surface level 20. The liquid 18 rises through the structure 901 above the level 20 to a top portion of the structure 901. A bent portion of the structure 901 directs liquid flow downward toward the discharge end 16. Siphoning takes over once liquid flow passes the liquid level 20 on the downside portion.

Treated liquid 28 exits the discharge end 16 into the lower vessel 24. At this point, in continuous operation mode, the valve 32 and a valve 40 (in an outlet 38) may be adjusted to maintain a desired flow rate. In one aspect, in a batch operation, the valve 32 remains closed until a new batch of liquid 18 is introduced to the system. The discharge end 16 may be left suspended over the vessel 24 so that liquid 28 falls from discharge end 16 into vessel 24. The liquid level 20 and the support 12 may be adjusted so that the bent portion of the structure 901 is in contact with the surface level 20.

The structure 901, as is true for any treatment structure according to the present invention, can be sized and/or configured in many forms and may have any cross-sectional area to fit any particular application, e.g., but not limited to, circular cross-section, cylindrically shaped, square shaped, or rectangularly shaped. Also, as is true for any treatment structure according to the present invention, the base material be made of a combination or composite of two, three or several materials having different characteristics to fit any particular application.

Optionally, as shown in FIG. 9, an enclosure 42 isolates an inner gaseous atmosphere 52 which contacts the structure 901 and the liquid 18. The enclosure 42 permits modification and control of the pressure, the temperature, and the composition of inner atmosphere 52. An inlet 48 may be provided to inject different compositions of liquid and/or gas, to attach a pump for changing the pressure of the gas between the housing and the medium, or to attach an apparatus 101 for control of the temperature within the enclosure (or for recirculation of gas). The temperature of the liquid can be raised, lowered, or maintained so that the liquid exiting from the outlet is at a desired temperature. By appropriate sizing of the treatment structure and its length above the liquid level, a desired amount of cooling can be effected.

The temperature control may take a variety of forms. It is shown as one which heats or cools, but it could take other forms such as heating and cooling coils surrounding a housing. Additionally, the pressure, temperature and composition of a gas in the enclosure may be controlled by a plurality of individual controls, or by a single control apparatus.

Although the ends 44 and 46 of the enclosure 42 are shown immersed in the liquids 18 and 26, this is only to provide a seal for the inner atmosphere 52. The enclosure is not intended to work as a siphon. In one aspect, the liquid does not flow through the inner space occupied by the atmosphere 52, but only through the structure 901. The enclosure 42 may take a variety of forms, and it may also completely enclose vessels 22 and 24. A separate container (shown by a rectangle in dotted lines) may be used to enclose both vessels 22 and 24 and the enclosure 42.

A power source V (shown schematically; like any power source disclosed herein) imposes a potential difference on the structure 901 (on substantially all of it or on a part or parts of it) so that, via the electrically conductive nanomaterial NM, a lethal current flows killing living thing(s) that pass through the structure 901.

Figure 10:
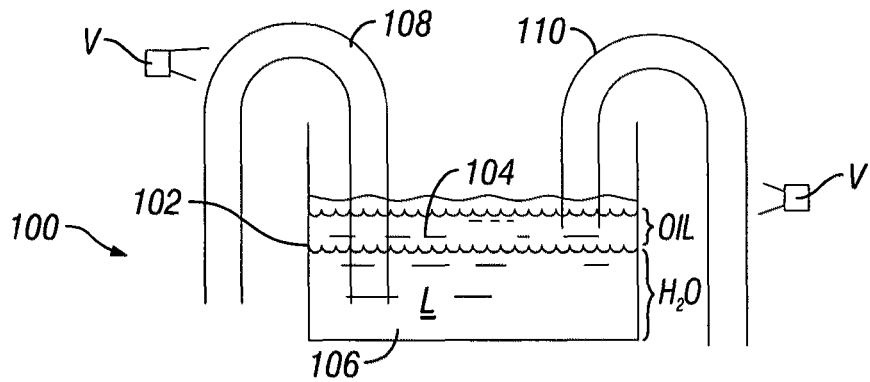
FIG. 10 is a schematic view of a system according to the present invention.

FIG. 10 illustrates a system 100 according to the present invention for treating a liquid L is oil and water in a two-phase liquid combination. The system 100 has a container 102 containing a two-phase liquid with one phase 104, an oil phase, above another phase 106, a water phase. A treatment structure 108 according to the present invention is primed with water prior to its insertion into the liquid and, extends through the oil 104 into the water 106. Another treatment structure 110 extends into the oil 104. The structure 110 transports treated oil from the container 102 and the structure 108 transports treated water from the container 102. Of course only one treatment structure may be employed to purify only one liquid or one liquid or more of a multi-phase combination may be treated by using the appropriate number of structures.

Power sources V (shown schematically; like any power source disclosed herein) impose a potential difference on their respective treatment structures 108, 110 (on substantially all of or on a part or parts of the treatment structure) so that, via the electrically conductive nanomaterial therein, a lethal current flows killing living thing(s) that pass through the structure.

Figure 11:
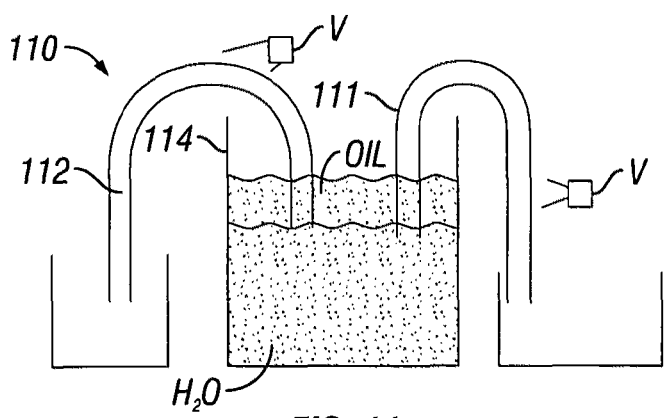
FIG. 11 is a schematic view of a system according to the present invention.

As shown in FIG. 11 two treatment structures 111 and 112 may be used to treat and remove water from a container 114 containing an emulsion of oil and water. The treatment structures 108, 110, 11, and 112 may be any structure disclosed herein according to the present invention. Power sources V (shown schematically; like any power source disclosed herein) impose a potential difference on their respective treatment structures 111,112 (on substantially all of or on a part or parts of the treatment structure) so that, via the electrically conductive nanomaterial therein, a lethal current flows killing living thing(s) that pass through the structure.

Figure 12:
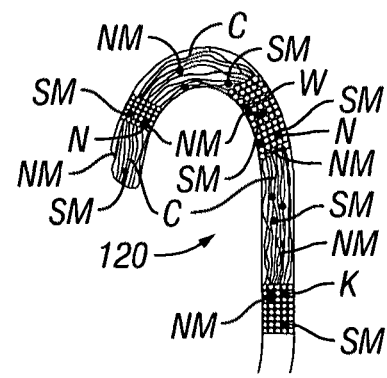
FIG. 12 is a schematic view of a system according to the present invention.

As shown in FIG. 12 a treatment structure 120 according to the present invention can include different base materials at different locations therein. For example, the structure 120 may have cotton C, wool W, ballistic material, Kevlar (trademark) material K, and nylon N. Of course, as desired different materials in different lengths and in different configurations may be present in different areas. Electrically conductive nanomaterial NM may be present in one, some, or all of these areas. Silver material SM may be present in one, some, or all of these areas.

Figure 13:
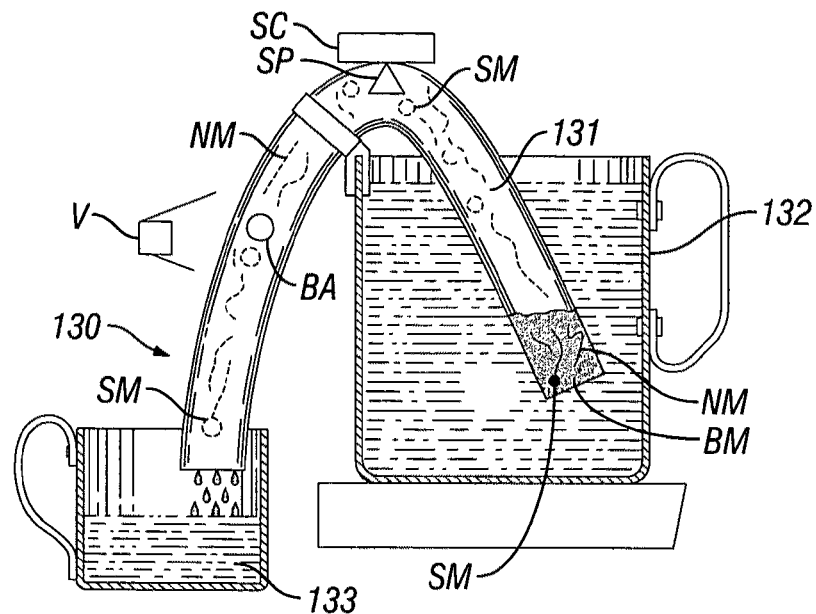
FIG. 13 is a schematic view of a system according to the present invention.

FIG. 13 discloses a system 130 according to the present invention which has a treatment structure 131 which may be like any treatment structure disclosed herein that has electrically conductive nanomaterial NM in base material BM, and, optionally, silver material SM. Optionally, the nanomaterial NM is electrically conductive nanomaterial with silver or silver material. Optionally, such materials are throughout the structure 131 or only in a part of or parts of the structure 131 (as may be true for any treatment structure according to the present invention). By siphon action, the treatment structure 131 conveys fluid, e.g., water, from a first container 132, e.g., a cup, to a second container 133, e.g., a cup, and the fluid is treated as it flows through the structure 131. A power source V (shown schematically; like any power source disclosed herein) impose a potential difference on the treatment structure 131 on substantially all of or on a part or parts of the treatment structure) so that, via the electrically conductive nanomaterial therein, a lethal current flows killing living thing(s) that pass through the structure.

Optionally, and as may be included with any treatment structure according to the present invention, a battery system BA connected to the structure 131 imposes a potential difference on substantially all or part of or parts of the structure 131; and/or optionally, and as may be included with any treatment structure according to the present invention, a solar power system SP connected to the structure 131 with a solar cell (or cells) SC imposes a potential difference on substantially all or part of or parts of the structure 131. Any power system used with the system 130 (or with any system according to the present invention), may supply sufficient power to heat the treatment structure, to heat fluid passing therethrough, to boil fluid therein, to boil water therein, and/or to kill undesirable things in fluid passing through the treatment structure.

Figure 14:
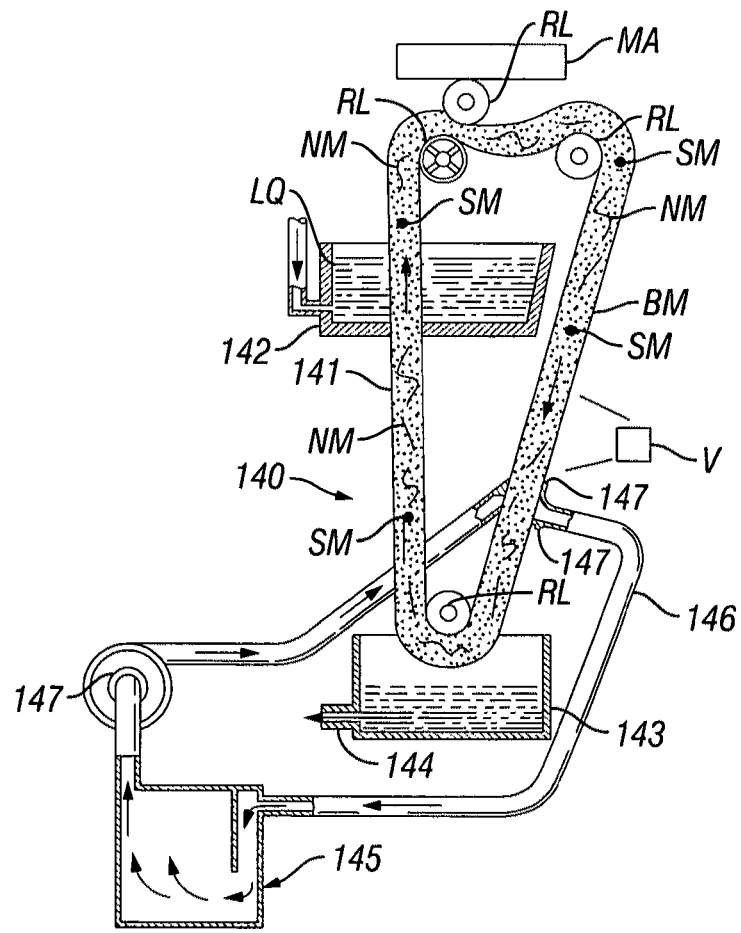
FIG. 14 is a schematic view of a system according to the present invention.

FIG. 14 discloses a system 140 according to the present invention which has a treatment structure 141 which may contain any electrically conductive material NM disclosed above, optionally any silver material SM disclosed above, and any base material BM disclosed above. A power source V (shown schematically; like any power source disclosed herein) impose a potential difference on the treatment structure 141 on substantially all of or on a part or parts of the treatment structure) so that, via the electrically conductive nanomaterial therein, a lethal current flows killing living thing(s) that pass through the structure. Multiple power sources V may be used with the structure 141.

A moving apparatus MA with rollers RL moves the treatment structure 141 through liquid LQ in a container 142 and then this liquid passes through part of the structure 141 and, as the structure 141 moves as indicated by the arrows therein, the treated liquid flows from the structure 141 into a container 143 from which it can be evacuated via an outlet 144. Optionally a system 145 with piping 146 and a pump 147 provides fluid (e.g., gas and/or liquid) that is pumped through the structure 141 for further treatment of fluid passing through the structure 141. The structure 141 moves through appropriate openings 147 in the piping 146. The fluid supplied by the system 145 may be any known fluid provided in known treatment and/or filtration systems.

Figure 15:
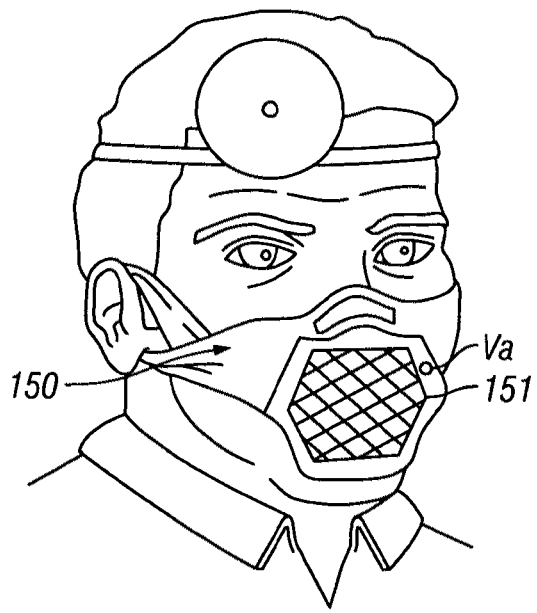
FIG. 15 is a perspective view of a person wearing a mask according to the present invention.

FIG. 15 shows a person wearing a mask 150 according to the present invention which has a treatment structure 151 (which may be like any treatment structure described above, e.g., but not limited to, as in FIGS. 1-13). A power source Va (like any power source described above, including, but not limited to, as in FIG. 13) provides power for producing a current across the structure 151. Suitable insulation is used to prevent the person from getting shocked.

Figure 16:
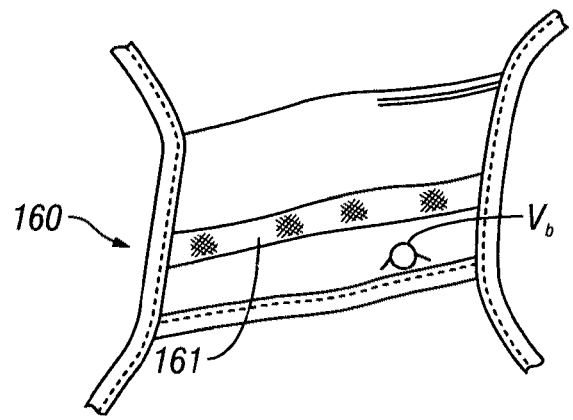
FIG. 16 is a perspective view of a mask according to the present invention.

FIG. 16 shows a mask 160 according to the present invention which has a treatment structure 161 (which may be like any treatment structure described above, e.g., but not limited to, as in FIGS. 1-13, 15). A power source Vb (like any power source described above, including, but not limited to, as in FIG. 13 or 15) provides power for producing a current across the structure 161. Suitable insulation is used to prevent a person wearing the mask from getting shocked.

Figure 17:
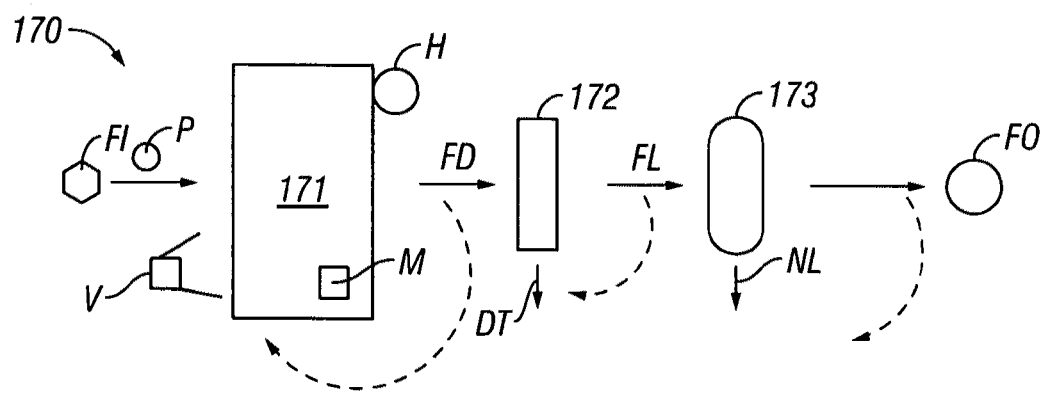
FIG. 17 is a schematic view of a fluid treatment system according to the present invention.

FIG. 17 shows a system 170 according to the present invention which has a treatment structure 171 according to the present invention which may be any treatment structure disclosed above with a power source V which may be any power source disclosed above. Input fluid FI with undesirable living thing(s) therein flows through and is treated by the treatment structure 171 so that the living thing(s) are killed.

Fluid with dead things FD (which may have nanomaterial therein from the structure 171) flows to an optional apparatus 172 which removes the dead things DT producing fluid FL. The fluid FL (or, optionally, the fluid FD) is fed to an apparatus 173 which removes nanomaterial NL from the fluid FL (or FD) producing output treated fluid FO free of dead things and/or free of at least some or substantially all of nanomaterial that was in the fluid FD.

It is within the scope of the present invention to include with any system according to the present invention and/or with any treatment structure according to the present invention an apparatus 172, an apparatus 173 and/or both such apparatuses. It is also within the scope of the present invention to recycle fluid from any step shown in FIG. 17 back to the system 170 and/or to any previous step in the system (indicated by the dotted lines beneath fluid FD, fluid FL, and adjacent the arrow indicating flow of the fluid FO). Optionally, the system 170 may include magnet(s) M, and/or magnet apparatus or apparatuses and/or heater(s) H used as described above.

It is within the scope of the present invention to pump fluid to a treatment structure according to the present invention, e.g., as shown in FIG. 17 fluid FI may, optionally, be pumped with a pump P to the treatment structure 171. In such embodiments, the treatment structure need not act as a non-gravity-feed fluid mover. Also, optionally, any suitable pump is used to feed the apparatuses 172 and 173.

Instead of or in addition to the silver material SM used in embodiments described above, a solution with silver particles, including, but not limited to, known colloidal silver solutions, (e.g., but not limited to, such solutions with a liquid suspension of microscopic silver particles with a concentration of 30 parts per million, less than 30 parts per million, 50 parts per million, or more) may be added to fluid or to a container with fluid to be treated by a treatment structure and/or system according to the present invention and/or to any container or housing in any system herein into which fluid is introduced before, during, or after treatment according to the present invention, including, but not limited to, into a container or housing into which fluid is gravity fed, upflowed, or siphoned. Optionally, any treatment structure disclosed herein may be soaked or primed with a silver solution, including, but not limited to, systems with treatment structures which act to siphon fluid which may be primed with such a silver solution.

The optional apparatus 172 may be any suitable known apparatus, machine, device or method for removing the dead things from the liquid; including, but not limited to, filters, porous membranes, centrifuges, skimmers, precipitation-based apparatuses and methods, density-differential separation systems and/or structures, and bottom sweepers; and may also include systems and methods for separating treated water from other things, e.g. distillation and condensation systems and methods which result in the fluid, e.g. water, being separated from the dead things.

The optional apparatus 173 may be any suitable known apparatus, machine, device or method for removing nanomaterial from liquid. The apparatus 173 may be or may employ the separation principles disclosed in any reference referred to herein, including, but not limited to, the following United States references, all fully incorporated herein, for all purposes and in the references cited in these references: U.S. Pat. Nos. 7,250,188; 7,815,806; 7,074,310; 7,727,505; 7,074,310; 7,514,063; and in U.S. Applications with publication numbers 2004/0232073; 2006/0054555; 2006/0062718; 2008/0290007; 2008/0260616; 2008/0063587; 2007/0269364; and 2007/0258880.

The electrically conductive nanomaterial used in embodiments of the present invention may be any electrically conductive nanomaterial in the references referred to in the previous paragraph and those disclosed in these U.S. patents and in these U.S. applications: U.S. Pat. Nos. 7,820,132; 7,812,083 and 7,670,831 and U.S. Applications publication numbers 2010/0288980; 2010/0173376; 2010/0160553; 2010/0158193; 2010/0140097; 2010/0068526; 2010/0012922; 2010/0000770; 2009/0314647; 2009/0311166; 2009/006846; 2009/0001326; 2008/0233396; 2008/0145300; 2008/0044651; 2008/0020130; 2007/0236325; 2006/0135030; 2006/0093642; 2004/0202603; 2003/0012723; 2004/0028901 and 2004/0235016 (all said references incorporated fully herein for all purposes). The silver material used in methods according to the present invention (e.g. the silver material SM in some drawings) may be any thing with silver disclosed in the references referred to in this paragraph or in the previous paragraph and/or in U.S. Pat. Nos. 7,820,292; 6,918,284; 7,355,216; and 7,820,291 and/or in U.S. Applications publication numbers 2005/0208304 and 2010/0000770 and in the references disclosed in these patents and in these published applications. Nanomaterial with silver therein, therewith, or thereon may be, but is not limited to, any nanomaterial with silver in any of the references in this paragraph or in the previous paragraph. In any embodiment herein, silver may be provided by connectors, wires, or leads used with an electrical power source, with the connectors, etc. in and/or exposed to liquid to be treated.

Figure 18A:
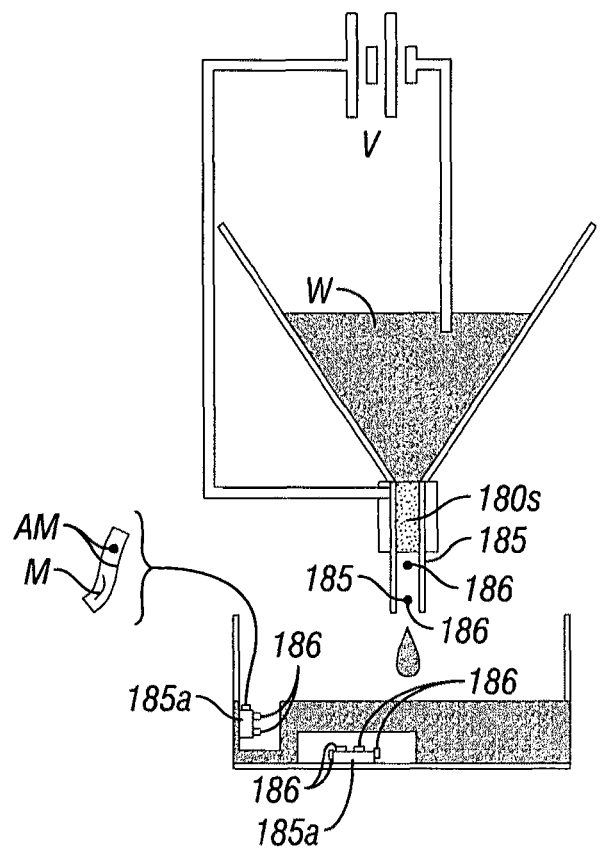
FIG. 18A is a schematic view of a fluid treatment system according to the present invention.
Figure 18B:
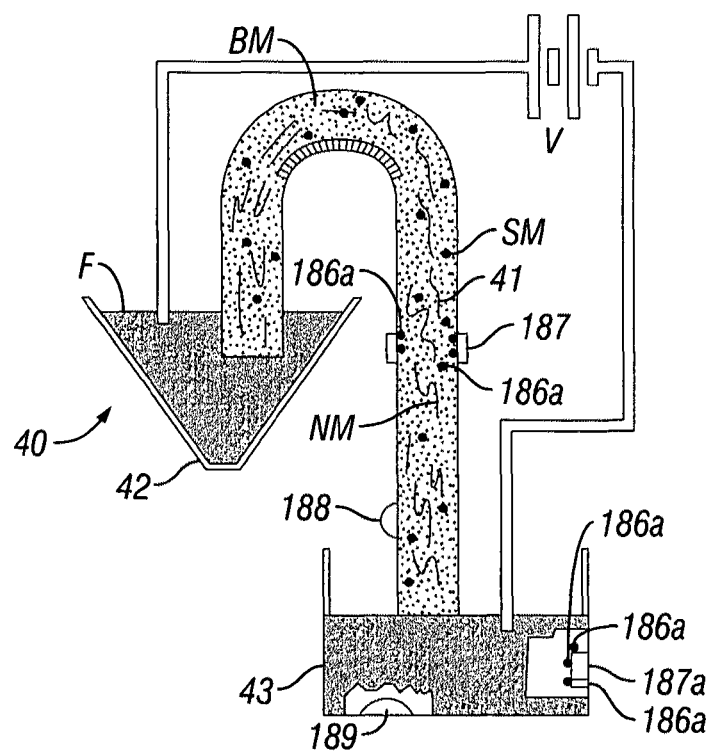
FIG. 18B is a schematic view of a fluid treatment system according to the present invention.

In one aspect, the nanomaterial has magnetically attractive material therein or thereon or combined therewith (e.g., in a fabric, mesh, intertwined material, material adhered together, bonded together, sintered together, connected together, tied together, or fused together as disclosed in any of the references in the previous two paragraphs) and a source of magnetism (any suitable known source) is used to attract the nanomaterial for removal from the liquid. As shown in FIG. 18A, magnet(s) 185 and/or magnet(s) 185a remove nanomaterial 186 (not to scale) from water W. The nanomaterial 186 is electrically conductive nanomaterial which includes magnetically attractive material MAM (not shown to scale). The magnet(s) may be spaced-apart; one magnet may be used (or one magnet system; the magnets may be in a liquid outlet and/or is a conduit; in a separate container; and/or they may in contact with or associated with a treatment structure according to the present invention. As shown in FIG. 18B, an electromagnet system 187 and/or 187a removes electrically conductive nanomaterial 186a (like numerals indicate like things in FIGS. 4 and 18A and 18B). Numeral 180s indicates a treatment structure according to the present invention (which may be any treatment structure according to the present invention). A power source 180v is used, but an power source disclosed herein may be used to impose a voltage so that current flows in the treatment structure.

It is within the scope of the present invention to pass sufficient current for a sufficient time period through any electrically conductive nanomaterial in any embodiment hereof so that the fluid with the nanomaterial is heated. In one particular aspect, the heating is sufficient to kill undesirable things in the fluid. In one aspect the fluid is water and the heating is sufficient to kill undesirable things in the water, and, in one particular aspect the heating is sufficient to boil the water. Any power source disclosed herein with suitable sensors and controls may be used for this purpose. Also, for example, as shown in FIG. 18B, a system 188 heats a portion of the treatment structure 41 to kill things therein and/or a system 189 heats fluid in the container 43 to kill things therein. Optionally a heater is used not to kill things, but to heat fluid in a treatment structure and/or in a container and/or in a conduit.

Figure 19A:
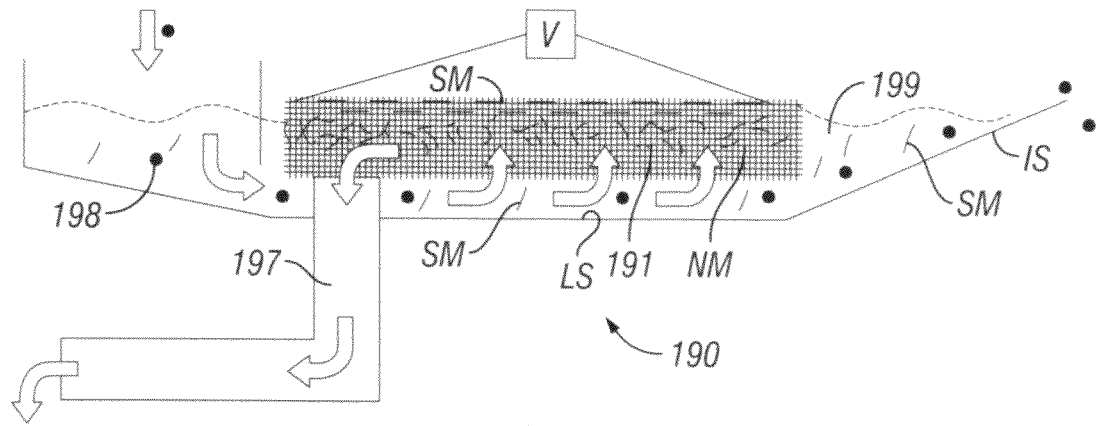
FIG. 19A is a schematic side cross-section view of a fluid treatment system according to the present invention.

Referring now to FIG. 19A a fluid to be treated, e.g., but not limited to, contaminated water with living things 198 (not to scale), is introduced into a pool 199 of a system 190 according to the present invention, and the fluid is forced through a screen 191 into a channel 197 that allows the screened fluid to flow via pipe work or channels to reservoirs or tanks (not shown) for subsequent use. Contaminants, dead things, and/or debris falls under gravity to a lower surface LS, from which they can be conveyed out from under the screen 191 by any suitable means or method, including, but not limited to, by vibration, by an auger, or via a moving belt. An optional inclined surface IS may be used to facilitate conveyance of contaminants, etc., out of the pool 199.

The screen 191 has electrically conductive nanomaterial NM therein and/or thereon (not shown to scale), or the screen is made of such material. Optionally the system 190 includes silver material SM on the screen, in liquid in the pool 199, or both. A system V imposes a potential difference across the screen 191 thereby applying a current to the nanomaterial NM which is sufficient to kill things in the fluid flowing through or into contact with the screen 191.

Figure 19B:
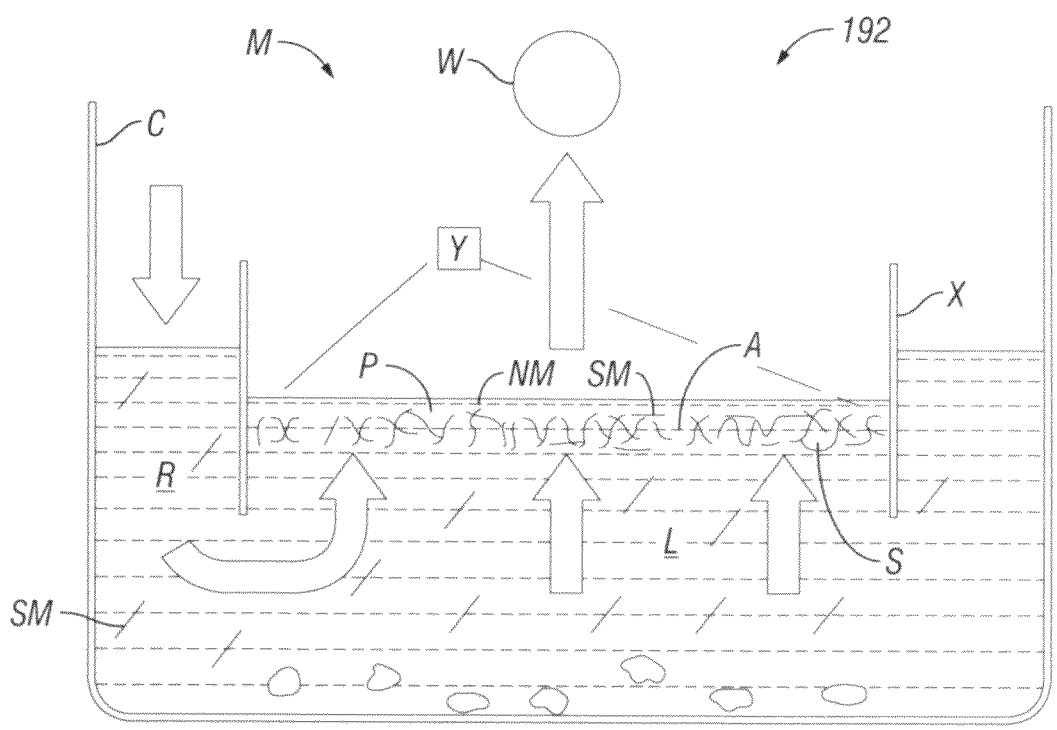
FIG. 19B is a schematic side cross-section view of a fluid treatment system according to the present invention.

FIG. 19B shows a system 192 according to the present invention which has a container C into which material R is introduced, e.g. the material including liquid L and living things S. The material R flows to a screen apparatus A which is mounted in a basket or box X. Part P of the material, e.g. liquid or liquid plus some dead things, flows up through the screen apparatus A. The part P is removed from the system by removal apparatus W (e.g. vacuum or pump apparatus). Part of the material, e.g. solids, dead things, and/or agglomerations or masses of solids, either settles down in the container C or, upon being prevented from further upward flow by the screen apparatus A and/or by material already adjacent the screen apparatus A, falls downwardly in the container C.

The screen apparatus A has electrically conductive nanomaterial NM therein and/or thereon (not shown to scale), or the screen is made of such material. Optionally the system 192 includes silver material SM on the screen apparatus, in liquid in the container C, or both. A system W imposes a potential difference across the screen apparatus thereby applying a current to the nanomaterial NM which is sufficient to kill things in the fluid flowing through or into contact with the screen apparatus. Any method or system herein may use a removal apparatus W to facilitate the movement, evacuation, or removal or treated fluid, e.g. but not limited to water treated to kill living things, for a flow stream or from a container. Instead of the screen 191 or the apparatus A, any treatment structure according to the present invention can be used with the systems 190 and 192.

Figure 20A:
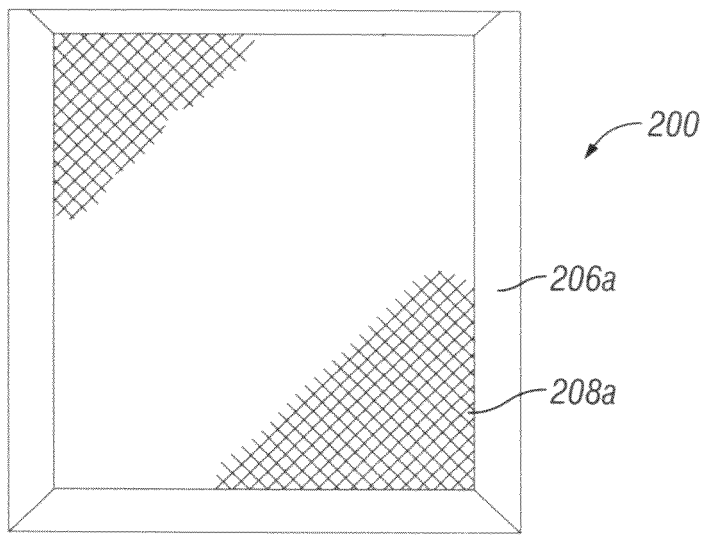
FIG. 20A is a front view of a fluid treatment system according to the present invention.
Figure 20B:
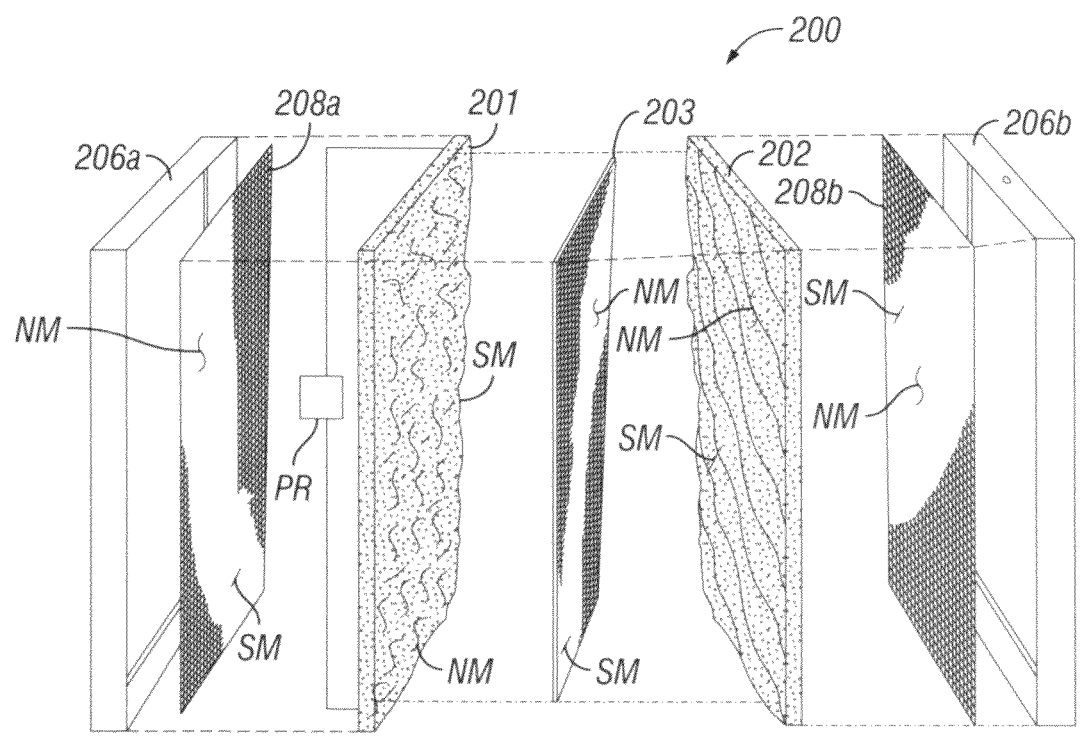
FIG. 20B is an exploded view of the fluid treatment system of FIG. 20A.

FIGS. 20A and 20B show a fluid treatment system 200 according to the present invention which has optional frames 206a and 206b, a sheet of material 201, a second optional sheet of material 202, an optional electrical conductive apparatus 203, an optional screen 208a, and an optional screen 208b. It is within the scope of the present invention for the material 201 to be of such a size and for openings through the material 201 to be of such a size that the material does not act as a filter, but simply allows fluid (air or liquid) to flow therethrough unimpeded (and this is true for the material 202). Alternatively, the material 201 may include any known filter material or media (as may the material 202).

The material 201 has electrically conductive nanomaterial NM therein, thereon, and/or combined therewith (nanomaterial not shown to scale), optionally, silver material SM. Optionally, the nanomaterial NM is electrically conductive nanomaterial with silver or silver material. Optionally, such materials are throughout the material 201 or only in a part of or parts of it. Fluid flows through the material 201 and the fluid is treated as it flows therethrough. A power source PS (shown schematically; like any power source disclosed herein) imposes a potential difference on the material 201 on substantially all of or on a part or parts of the material so that, via the electrically conductive nanomaterial therein, a lethal current flows killing living thing(s) that pass through the material 201.

Optionally, the material 201 contains silver material SM which may be any silver material disclosed herein. Optionally, the material 202, the screens 208a and 208b, and/or the apparatus 203 may have nanomaterial NM and/or silver material SM as described for the material 201.

Optionally, a power source PR (like any disclosed herein) imposes a potential difference across the material 201. Optionally, the material 202 may also have its own dedicated power source like the power source PR. Optionally, the screemn 208A and/or the screen 208b may also have its own dedicated power source like the power source PR. Optionally the apparatus 203 is like the electrical conductive means disclosed in U.S. Pat. No. 5,807,425 (incorporated fully herein for all purposes).

Figure 21:
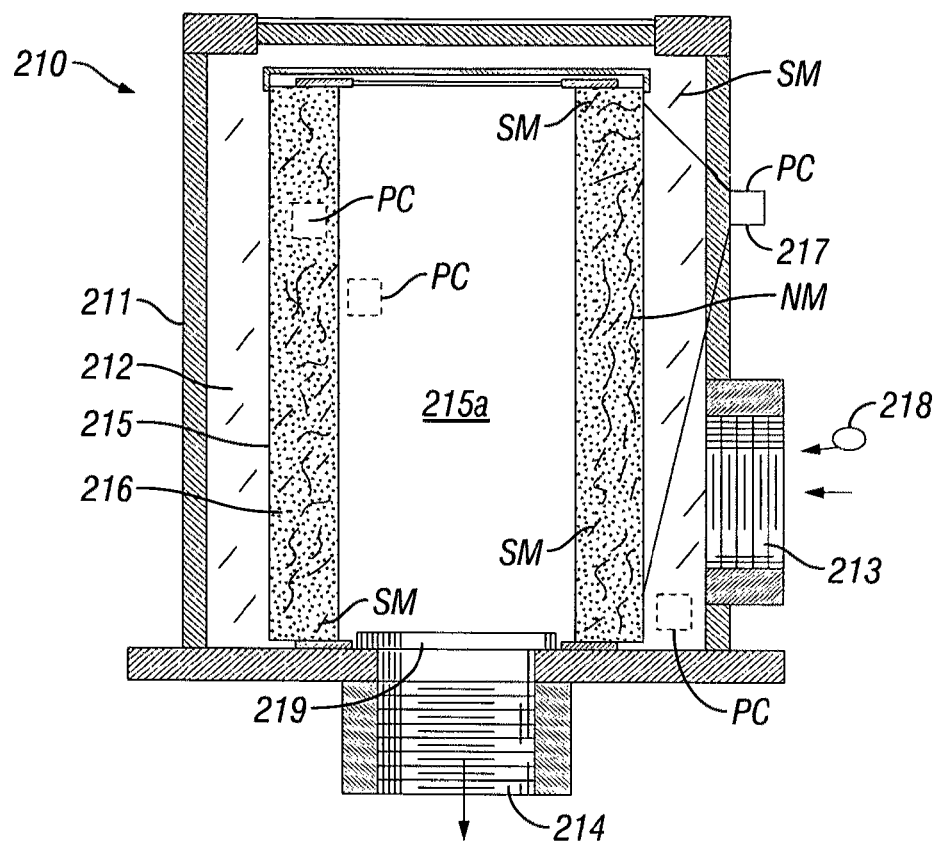
FIG. 21 is a schematic side cross-section view of a fluid treatment system according to the present invention.

FIG. 21 illustrates a system 210 according to the present invention which has a housing 211 with an inlet 213 through which fluid flows to an interior of the housing 211 and an outlet 214 from which treated fluid flows out from the housing 211. A filter cartridge 215 is mounted within the interior 212 of the housing 211 with a filter outlet 219 in fluid communication with the housing outlet 214 so that fluid treated by the filter cartridge 215 can flow out from the filter cartridge into the outlet 214.

The filter cartridge 215 has filter material 216 (which is any known suitable filter material for filtering a fluid, e.g., a gas, a liquid, or a combination thereof). Fluid flows through the filter material 216 which filters out things of a desired size and then filtered fluid flows into an interior 215a from which it flows to the filter cartridge outlet 219. Optionally, the filter material fills the filter cartridge. The housing 211, inlet 213, outlet 214, outlet 219, and the general overall shape of the filter cartridge 215 may be any desired shape and, in one aspect, each of these is generally circular in cross-section.

The filter material 216 contains nanomaterial NM (not shown to scale) which is present in sufficient amounts and is sufficiently dispersed so that, when a potential difference is imposed thereon by a power source 217 (labeled "PC"), current flows of sufficient power to kill live things in fluid being filtered. The nanomaterial NM may be any electrically conductive nanomaterial disclosed herein. Optionally the filter material 216 also has silver material SM therein (not shown to scale) which may be any silver or silver material disclosed herein. In one aspect, such a filter system is provided in which the nanomaterial is not used. Optionally, silver material SM is provided in the fluid flowing into the housing by a system 218 (e.g., but not limited to, a silver solution, e.g, but not limited to, a colloidal silver solution). Any system herein according to the present invention may have a system like the system 218 for providing silver for a fluid in a container or injection into a treatment structure.

The power source 217 may be located as indicated in FIG. 21; or it may be located within a housing (shown by a power source in dotted line within the housing 211) or within filter material (or within base material in other systems) and the power source may be any type disclosed herein, including, but not limited to, solar power systems, generators, and batteries.

The present invention, therefore, provides, in at least certain embodiments, a treatment structure or apparatus, and/or a method for treating a fluid, the method using the treatment structure and including: passing fluid (e.g., gas, water, or a mixture thereof) through a treatment structure, the fluid containing undesirable living things, the treatment structure having electrically conductive nanomaterial with silver; containing electrically conductive nanomaterial with silver; flowing an electric current in the fluid in the treatment structure via the electrically conductive nanomaterial with silver or silver material to kill undesirable living things in the treatment structure; and killing undesirable things in the fluid. Such a method may include one or some, in any possible combination, of the following: wherein the fluid is water; wherein the fluid passes through the treatment structure by the force of gravity; wherein the fluid passes through the treatment structure by siphoning, pumping, and/or upflow; wherein the treatment structure is moved through the fluid so that the treatment structure takes in fluid and said fluid passes through the treatment structure for treating thereby; wherein electric current flows through substantially all of the treatment structure; wherein electric current flows through a portion of the treatment structure; wherein the treatment structure contains base material and the electrically conductive nanomaterial with silver or silver material is in the base material; wherein the base material is one of nylon, plastic, fibers, granular media, fabric, fibril materials, filamentous materials, Kevlar, ballistic material, inorganic or organic materials, biological organism selective materials, natural or synthetic materials, cotton, wool, polyester, fiber glass, metal, woven or nonwoven, air laid web material, sheets of material, interleaved sheets, material with pores or openings or pore sizes such that it does not filter fluid or material with pores or openings or pore sizes of such dimensions that fluid is filtered, material containing silver and/or silver material; wherein the base material contains silver and/or silver material; wherein the nanomaterial is one of nanotubes, nanorods, nanowires, nanoparticles, nanostructures, nanofibers, nanofabric, nanocylinders, nanographene, nanographene ribbons, transformed nanomaterials, functionalized nanomaterial, metallized nanomaterial, carbon nanomaterials, carbon nanotubes, single walled nanotubes, multi-walled nanotubes, functionalized nanotubes and metallized nanotubes; flowing treated fluid from the treatment structure; wherein the treated fluid contains dead things killed in the treatment structure, the method further including removing dead things from the treated fluid; wherein the treated fluid contains nanomaterial, the method further including removing nanomaterial from the treated fluid; wherein the removed nanomaterial contains magnetically attractive material, the method further including removing the nanomaterial containing magnetically attractive material with one of at least one magnet, a plurality of magnets, at least one magnet apparatus, and a plurality of magnet apparatuses; wherein the magnet apparatus is one of an electromagnet apparatus, at least one electromagnet apparatus, and a plurality of electromagnet apparatuses; wherein magnet apparatus is within the treatment structure, adjacent the treatment structure, within a member through which the treated fluid passes, or within a container containing the treated fluid; wherein the electric current heats fluid in the treatment structure; wherein the electric current boils fluid in the treatment structure; wherein the electric current heats fluid in the treatment structure thereby killing living things in the fluid; wherein a power source imposes a potential difference across the nanomaterial so that the electric current flows, the power source location being one of outside a container with the nanomaterial therein, within the nanomaterial, within base material, within filter material, adjacent nanomaterial, adjacent filter material, said power source including connectors for connection to impose the potential difference; and/or wherein the electric current is provided by a power source that is one of generator, solar power system, and battery.

The present invention, therefore, provides in some, but not necessarily all, embodiments treatment structures and methods for treating a fluid, the method including: passing fluid through a treatment structure, the fluid containing undesirable living things, the treatment structure containing electrically conductive nanomaterial with silver or silver material; flowing an electric current in the fluid in the treatment structure via the electrically conductive nanomaterial with silver to kill undesirable living things in the treatment structure; killing undesirable things in the treatment structure producing treated fluid; flowing the treated fluid back to the treatment structure; passing the treated fluid through the treatment structure; flowing an electric current in the treated fluid in the treatment structure via the electrically conductive nanomaterial with silver or silver material to kill undesirable living things in the treatment structure.

The present invention, therefore, provides in some, but not necessarily all, embodiments treatment structures and methods for treating a fluid, the methods including: passing fluid through a treatment structure, the fluid containing undesirable living things, the treatment structure containing electrically conductive nanomaterial, the fluid containing silver or silver material; flowing an electric current in the fluid in the treatment structure via the electrically conductive nanomaterial to kill undesirable living things in the treatment structure; and killing undesirable things in the treatment structure, wherein the fluid is moved through the treatment structure by siphoning or by pumping or wherein the treatment structure is moved through the fluid. Such a treatment structure and such a method may include the electrically conductive nanomaterial including electrically conductive nanomaterial with silver.

The present invention, therefore, provides in some, but not necessarily all, embodiments treatment structures and methods for treating a fluid, the methods including: passing fluid through a treatment structure, the fluid containing undesirable living things, the treatment structure containing electrically conductive nanomaterial, the fluid containing silver or silver material; flowing an electric current in the fluid in the treatment structure via the electrically conductive nanomaterial silver to kill undesirable living things in the treatment structure, the electric current passing through only a portion of the treatment structure; and killing undesirable things in the treatment structure. In such a method and such a structure the electrically conductive nanomaterial includes electrically conductive nanomaterial with silver or silver material.

The present invention, therefore, provides in some, but not necessarily all, embodiments treatment structures and methods for treating a fluid, the methods including: passing fluid through a treatment structure, the fluid containing undesirable living things, the treatment structure containing electrically conductive nanomaterial, the fluid containing silver or silver material; flowing an electric current in the fluid in the treatment structure via the electrically conductive nanomaterial silver to kill undesirable living things in the treatment structure; killing undesirable things in the treatment structure; flowing treated fluid from the treatment structure; and removing dead things from the treated fluid and/or removing nanomaterial from the treated fluid. In such a structure and in such a method the electrically conductive nanomaterial includes electrically conductive nanomaterial with silver or silver material.

The present invention, therefore, provides in some, but not necessarily all, embodiments treatment structures and methods for treating a fluid, the methods including: passing fluid through a treatment structure, the fluid containing undesirable living things, the treatment structure containing electrically conductive nanomaterial, the fluid containing silver or silver material; flowing an electric current in the fluid in the treatment structure via the electrically conductive nanomaterial silver to kill undesirable living things in the treatment structure; and/or killing undesirable things in the treatment structure, and/or removing nanomaterial and/or silver material from the treated fluid. Such a treatment structure and/or such a method may include one or some, in any possible combination, of the following: the electrically conductive nanomaterial includes electrically conductive nanomaterial with silver or silver material; the removed nanomaterial contains magnetically attractive material, the method further including removing the nanomaterial containing magnetically attractive material with magnet apparatus; wherein the magnet apparatus is one of magnet, at least one magnet, a plurality of magnets, an electromagnet apparatus, at least one electromagnet apparatus, and a plurality of electromagnet apparatuses; and/or the magnet apparatus is within the treatment structure, adjacent the treatment structure, within a member through which the treated fluid passes, or within a container containing the treated fluid.

The present invention, therefore, provides in some, but not necessarily all, embodiments treatment structures and methods for treating a fluid, the methods including: passing fluid through a treatment structure, the fluid containing undesirable living things, the treatment structure containing electrically conductive nanomaterial, the fluid containing silver or silver material; flowing an electric current in the fluid in the treatment structure via the electrically conductive nanomaterial silver to kill undesirable living things in the treatment structure; killing undesirable things in the treatment structure; wherein the electric current heats the electrically conductive nanomaterial which heats fluid in the treatment structure. Such a structure and such a method may include one or some, in any possible combination, of the following: the electric current boils fluid in the treatment structure; the electric current heats fluid in the treatment structure thereby killing living things in the fluid; and/or the electrically conductive nanomaterial includes electrically conductive nanomaterial with silver or silver material.

The present invention, therefore, provides in some, but not necessarily all, embodiments treatment structures and methods for treating a fluid, the methods including: passing fluid through a treatment structure, the fluid containing undesirable living things, the treatment structure containing electrically conductive nanomaterial; flowing an electric current in the fluid in the treatment structure via the electrically conductive nanomaterial material to kill undesirable living things in the treatment structure; killing undesirable things in the treatment structure producing treated fluid; flowing the treated fluid back to the treatment structure; passing the treated fluid through the treatment structure; flowing an electric current in the treated fluid in the treatment structure via the electrically conductive nanomaterial to kill undesirable living things in the treatment structure. In such a method, optionally the electrically conductive nanomaterial includes electrically conductive nanomaterial with silver or silver material.

The present invention, therefore, provides in some, but not necessarily all, embodiments treatment structures and methods for treating a fluid, the methods including: a treatment structure for treating fluid, e.g., but not limited to water, air, and liquid, the treatment structure including: base material; electrically conductive nanomaterial including electrically conductive nanomaterial with silver or silver material. Such a structure may include a power source for applying current to the electrically conductive nanomaterial with silver or silver material to kill things in the fluid, e.g., but not limited to a solar power apparatus, generator, or battery and/or the structure may be a liquid filter or an air filter.

The present invention, therefore, provides in some, but not necessarily all, embodiments treatment structures and methods for treating a fluid, the methods including: passing fluid up through a treatment structure, the fluid containing undesirable living things, the treatment structure containing electrically conductive nanomaterial; flowing an electric current in the fluid in the treatment structure via the electrically conductive nanomaterial silver to kill undesirable living things in the treatment structure; and killing undesirable things in the treatment structure. In such a method a removal apparatus may facilitate flow of fluid from the treatment structure; the removal apparatus may be one of pump and vacuum apparatus; the treatment structure may be one or two or more screen apparatuses; at least one of the treatment structure and the fluid may contain silver material; the treatment structure may be a filter; and/or a power source may impose a potential difference across the nanomaterial so that the electric current flows, the power source location being one of outside a housing containing the treatment structure therein, within material in the housing that contains the nanomaterial, and within the housing but not within the material that contains the nanomaterial.

In conclusion, therefore, it is seen that the present invention and the embodiments disclosed herein and those covered by the appended claims are well adapted to carry out the objectives and obtain the ends set forth. Certain changes can be made in the subject matter without departing from the spirit and the scope of this invention. It is realized that changes are possible within the scope of this invention and it is further intended that each element or step recited herein is to be understood as referring to the step literally and/or to all equivalent elements or steps. It is intended to cover the invention as broadly as legally possible in whatever form it may be utilized. The invention described herein is new and novel in accordance with 35 U.S.C. §102 and satisfies the conditions for patentability in §102. The invention described herein is not obvious in accordance with 35 U.S.C. §103 and satisfies the conditions for patentability in §103. The inventor may rely on the Doctrine of Equivalents to determine and assess the scope of the invention. All patents and applications identified herein are incorporated fully herein for all purposes. The word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

What is claimed is:

1. A method for treating a fluid, the method comprising passing the fluid through a treatment structure, the fluid containing undesirable living things, the treatment structure containing electrically conductive nanomaterial, flowing an electric current in the fluid in the treatment structure via the electrically conductive nanomaterial to kill the undesirable living things in the fluid, and killing the undesirable living things in the fluid, and wherein heat generated by flow of the electric current boils the fluid in the treatment structure.

2. A method for treating a fluid, the method comprising passing the fluid through a treatment structure, the fluid containing undesirable living things, the treatment structure containing electrically conductive nanomaterial, flowing an electric current in the fluid in the treatment structure via the electrically conductive nanomaterial to kill the undesirable living things in the fluid, and killing the undesirable living things in the fluid, and wherein the electric current heats the fluid in the treatment structure thereby killing the undesirable living things in the fluid.

3. The method of claim 2 wherein the fluid contains silver material.

4. The method of claim 2 wherein the electrically conductive nanomaterial includes silver or silver material.

5. The method of claim 2 wherein the fluid is water.

6. The method of claim 2 wherein the fluid passes through the treatment structure by siphoning.

7. The method of claim 2 wherein the electrically conductive nanomaterial is one of nanotubes, nanorods, nanowires, nanoparticles, nanostructures, nanofibers, nanofabric, nanocylinders, nanographene, nanographene ribbons, transformed nanomaterials, functionalized nanomaterial, metallized nanomaterial, carbon nanomaterials, carbon nanotubes, single walled nanotubes, multi-walled nanotubes, functionalized nanotubes and metallized nanotubes.

8. The method of claim 2 wherein a power source imposes a potential difference across the electrically conductive nanomaterial so that the electric current flows, the power source being at a location being one of: outside a container with the electrically conductive material therein, within the electrically conductive nanomaterial, within a base material, within a filter material, adjacent the electrically conductive nanomaterial, adjacent a filter material, said power source including connectors for connection to impose the potential difference.

9. The method of claim 2 wherein the electric current flows in a path, the path being one of: a path through substantially all of the treatment structure and a path through a portion of the treatment structure.

10. The method of claim 2 wherein treated fluid is produced that contains dead things killed in the treatment structure, the method further comprising removing the dead things from the treated fluid.

11. The method of claim 2 wherein treated fluid contains the electrically conductive nanomaterial, the method further comprising removing the electrically conductive nanomaterial from the treated fluid.

12. A method for treating a fluid, the method comprising passing the fluid through a treatment structure, the fluid containing undesirable living things, the treatment structure containing electrically conductive nanomaterial, flowing an electric current in the fluid in the treatment structure via the electrically conductive nanomaterial to kill the undesirable living things in the fluid, and killing the undesirable living things in the fluid,
wherein the electrically conductive nanomaterial contains a magnetically attractive material, and removing the electrically conductive nanomaterial containing the magnetically attractive material with a magnet apparatus.

13. The method of claim 11 wherein the magnet apparatus is in a location which is one of: within the treatment structure, adjacent the treatment structure, within a member through which treated fluid passes, or within a container containing treated fluid.

* * * * *